United States Patent
Christie et al.

(10) Patent No.: US 11,542,518 B2
(45) Date of Patent: Jan. 3, 2023

(54) METHODS FOR OPTOGENETIC MANIPULATION OF STOMATAL FUNCTION

(71) Applicant: UNIVERSITY COURT OF THE UNIVERSITY OF GLASGOW, Glasgow (GB)

(72) Inventors: John Christie, Glasgow (GB); Mike Blatt, Glasgow (GB)

(73) Assignee: UNIVERSITY COURT OF THE UNIVERSITY OF GLASGOW, Glasgow (GB)

( * ) Notice: Subject to any disclaimer, the term of this patent is extended or adjusted under 35 U.S.C. 154(b) by 0 days.

(21) Appl. No.: 17/431,984

(22) PCT Filed: Feb. 19, 2020

(86) PCT No.: PCT/GB2020/050400
§ 371 (c)(1),
(2) Date: Aug. 18, 2021

(87) PCT Pub. No.: WO2020/169973
PCT Pub. Date: Aug. 27, 2020

(65) Prior Publication Data
US 2022/0042026 A1 Feb. 10, 2022

(30) Foreign Application Priority Data
Feb. 19, 2019 (GB) .................... 1902253

(51) Int. Cl.
*C12N 15/82* (2006.01)

(52) U.S. Cl.
CPC ..... *C12N 15/8225* (2013.01); *C12N 15/8273* (2013.01)

(58) Field of Classification Search
None
See application file for complete search history.

(56) References Cited

PUBLICATIONS

Wang et al. "Overexpression of plasma membrane H+-ATPase in guard cells promotes light-induced stomatal opening and enhances plant growth". PNAS. 111(1):533-538 (Year: 2014).*
Shi et al. Journal of Experimental Botany. "Cellular and molecular insight into the inhibition of primary root growth of *Arabidopsis* induced by peptaibols, a class of linear peptide antibiotics mainly produced by *Trichoderma* spp." 67 (8):2191-2205 (Year: 2016).*
Lawson T., "Stomatai Size, Speed, and Responsiveness Impact on Photosynthesis and Water Use Efficiency", Plant Physiology, Apr. 2014, pp. 1556-1570, vol. 164, No. 4.
(Continued)

*Primary Examiner* — Matthew R Keogh
*Assistant Examiner* — David R Byrnes
(74) *Attorney, Agent, or Firm* — Greer, Burns & Crain, Ltd.

(57) ABSTRACT

The invention relates to methods of increasing stomatal function in plants, which as a result leads to an increase in carbon assimilation and/or water use efficiency and ultimately an increase in yield. In particular the methods of the invention relate to the expression of light-gated potassium channels in the stomatal complex. Also described are genetically altered plants characterised by the above phenotype as well as methods of producing such plants.

14 Claims, 13 Drawing Sheets

Specification includes a Sequence Listing.

(56) References Cited

PUBLICATIONS

Wang, Y et al., "Overexpression of plasma membrane H+-ATPase in guard cells promotes light-induced stomatal opening and enhances plant growth", Proceedings of the National Academy of Sciences, Jan. 7, 2014, p. 533-538, vol. 111, No. 1.

Mcausland, L., et al., "Effects of kinetics of light-induced stomatal responses on photosynthesis and water-use efficiency", New Phytologist, Sep. 27, 2016, pp. 1209-1220, vol. 211, No. 4.

Consenting, C., et al., "Engineering of a light-gated potassium channel", Science, May 8, 2015, pp. 707-710, vol. 348, No. 6235.

Papanatsiou, M., et al., "Optogenetic manipulation of stomatal kinetics improves carbon assimilation, water use, and growth", Mar. 29, 2019, p. 1456-1459, vol. 363.

Lebaudy, A., et al., "Plant adaptation to fluctuating environment and biomass production are strongly dependent on guard cell potassium channels" PNAS, Apr. 1, 2008, pp. 5271-5276, vol. 105, No. 13.

PCT Notification of Transmittal of the International Search Report and the Written Opinion of the International Searching Authority, or the Declaration dated May 7, 2020 for PCT Application No. PCT/GB2020/050400.

\* cited by examiner

Figure 4

|  |  | Blue light ON | | Blue light OFF | |
|---|---|---|---|---|---|
|  |  | Max. Stomatal Conductance (mol m$^{-2}$ s$^{-1}$) | Opening Halftime (min) | Min. Stomatal Conductance (mol m$^{-2}$ s$^{-1}$) | Closing Halftime (min) |
| Dark – Blue Light Response | wt | 0.49 ±0.03 | 40.32 ±2.65 | 0.28 ±0.05 | 4.94 ±0.48 |
| | #1 | 0.50 ±0.03 | 22.94 ±0.34 ($P<0.001$) | 0.22 ±0.03 | 3.64 ±0.34 ($P=0.03$) |
| | #2 | 0.59 ±0.04 | 23.90 ±6.09 ($P=0.045$) | 0.22 ±0.03 | 3.18 ±0.47 ($P=0.019$) |
| Red – Blue Light Response | wt | 0.46 ±0.05 | 24.46 ±7.39 | 0.22 ±0.03 | 4.41 ±0.77 |
| | #1 | 0.50 ±0.09 | 6.69 ±1.06 ($P=0.012$) | 0.20 ±0.04 | 1.81 ±0.48 ($P=0.013$) |
| | #2 | 0.38 ±0.04 | 6.37 ±1.23 ($P=0.007$) | 0.20 ±0.03 | 2.98 ±0.39 ($P=0.045$) |

Figure 5

| | | wt | wt-BLINK #1 | wt-BLINK #2 | plp2 | plp2-BLINK #1 | plp2-BLINK #2 |
|---|---|---|---|---|---|---|---|
| LWL (75 μmol m⁻² s⁻¹) | Fresh Weight (g) | 0.94 ±0.09 | 1.21 ±0.17 | 1.12 ±0.09 | 0.41 ±0.05 | 0.39 ±0.08 | 0.44 ±0.05 |
| | Dry Weight (g) | 0.11 ±0.02 | 0.14 ±0.01 | 0.10 ±0.02 | 0.04 ±0.005 | 0.05 ±0.01 | 0.04 ±0.01 |
| | Rosette Area (cm²) | 36.26 ±3.40 | 36.00 ±1.87 | 43.85 ±1.95 | 13.67 ±2.22 | 9.72 ±0.90 | 13.83 ±1.75 |
| | WUEi (μmol of $CO_2$/mmol of $H_2O$) | 2.36 ±0.36 | 2.73 ±0.36 | 2.47 ±0.27 | - | - | - |
| | WUE (g/L of $H_2O$) | 4.52 ±0.60 | 5.43 ±0.48 | 4.00 ±0.32 | 1.46 ±0.22 | 1.81 ±0.43 | 1.72 ±0.33 |
| | FW:DW | 8.56 ±0.18 | 8.64 ±0.16 | 11.2 ±0.13 (P<0.001) | 10.25 ±0.02 | 7.80 ±0.04 | 11.00 ±0.06 |
| HWL (200 μmol m⁻² s⁻¹) | Fresh Weight (g) | 2.00 ±0.25 | 2.07 ±0.21 | 2.16 ±0.14 | 1.00 ±0.07 | 0.72 ±0.14 | 0.76 ±0.13 |
| | Dry Weight (g) | 0.16 ±0.02 | 0.17± 0.01 | 0.17 ±0.007 | 0.08 ±0.02 | 0.06 ±0.01 | 0.05 ±0.02 |
| | Rosette Area (cm²) | 68.31 ±5.09 | 58.11 ±9.08 | 62.62 ±2.62 | 24.26 ±1.15 | 21.27 ±3.60 | 19.60 ±2.18 |
| | WUEi (μmol of $CO_2$/mmol of $H_2O$) | 2.58 ±0.30 | 2.62 ±0.45 | 2.36 ±0.10 | - | - | - |
| | WUE (g/L of $H_2O$) | 6.23 ±0.84 | 6.66 ±0.46 | 6.69 ±0.29 | 3.29 ±0.80 | 2.07 ±0.53 | 1.85 ±0.30 |
| | FW:DW | 12.5 ±0.016 | 12.18 ±0.01 | 12.71 ±0.004 | 12.5 ±0.06 | 12.00 ±0.03 | 15.2 ±0.16 |

Figure 5 continued

| | | wt | wt-BLINK #1 | wt-BLINK #2 | plp2 | plp2-BLINK #1 | plp2-BLINK #2 |
|---|---|---|---|---|---|---|---|
| Fluctuating white light (water-sufficient) | Fresh Weight (g) | 0.66 ±0.02 | 0.77 ±0.07 (P<0.001) | 0.72 ±0.06 (P=0.001) | 0.34 ±0.01 | 0.45 ±0.05 | 0.39 ±0.05 |
| | Dry Weight (g) | 0.082 ±0.005 | 0.13 ±0.002 (P<0.001) | 0.12 ±0.003 (P<0.001) | 0.05 ±0.01 | 0.09 ±0.03 | 0.07 ±0.02 |
| | Rosette Area (cm$^2$) | 23.87 ±1.13 | 28.72 ±1.67 (P=0.027) | 27.28 ±1.45 (P=0.048) | 11.06 ±0.72 | 13.77 ±0.73 | 12.83 ±0.96 |
| | WUEi (μmol of $CO_2$/mmol of $H_2O$) | 1.72 ±0.15 | 1.92 ±0.08 | 1.89 ±0.05 | - | - | - |
| | WUE (g/L of $H_2O$) | 2.67 ±0.16 | 4.19 ±0.08 (P<0.001) | 4.15 ±0.10 (P<0.001) | 2.18 ±0.57 | 2.78 ±0.79 | 2.84 ±0.78 |
| | FW:DW | 8.054 ±0.001 | 5.926 ±0.008 (P<0.001) | 6.006 ±0.007 (P<0.001) | 6.80 ±0.04 | 5.00 ±0.11 | 5.57 ±0.08 |
| Fluctuating white light (water-limited) | Fresh Weight (g) | 0.60 ±0.005 | 0.75 ±0.09 | 0.71 ±0.003 | - | - | - |
| | Dry Weight (g) | 0.064 ±0.003 | 0.121 ±0.001 (P<0.001) | 0.11 ±0.01 (P=0.003) | - | - | - |
| | Rosette Area (cm$^2$) | 26.78 ±1.18 | 26.18 ±0.69 | 28.07 ±1.01 | - | - | - |
| | WUE (g/L of $H_2O$) | 2.08 ±0.11 | 3.66 ±0.03 (P<0.001) | 3.52 ±0.32 (P=0.008) | - | - | - |
| | FW:DW | 9.46 ±0.08 | 6.47 ±0.09 (P<0.001) | 6.81 ±0.03 (P<0.001) | - | - | - |

SEQUENCE LISTING

<160> NUMBER OF SEQ ID NOS: 25

<210> SEQ ID NO 1
<211> LENGTH: 92
<212> TYPE: PRT
<213> ORGANISM: Artificial Sequence
<220> FEATURE:
<223> OTHER INFORMATION: Kcv

<400> SEQUENCE: 1

Val Phe Ser Lys Phe Leu Thr Arg Thr Glu Pro Phe Met Ile His Leu
1               5                   10                  15

Phe Ile Leu Ala Met Phe Val Met Ile Tyr Lys Phe Phe Pro Gly Gly
            20                  25                  30

Phe Glu Asn Asn Phe Ser Val Ala Asn Pro Asp Lys Lys Ala Ser Trp
        35                  40                  45

Ile Asp Cys Ile Tyr Phe Gly Val Thr Thr His Ser Thr Val Gly Phe
    50                  55                  60

Gly Asp Ile Leu Pro Lys Thr Gly Ala Lys Leu Cys Thr Ile Ala
65                  70                  75                  80

His Ile Val Thr Val Phe Phe Ile Val Leu Thr Leu
                85                  90

<210> SEQ ID NO 2
<211> LENGTH: 279
<212> TYPE: DNA
<213> ORGANISM: Artificial Sequence
<220> FEATURE:
<223> OTHER INFORMATION: Kcv

<400> SEQUENCE: 2

```
gtgtttagta aatttctaac gcgaactgaa ccattcatga tacatctctt tattctcgca      60
atgttcgtga tgatctataa attcttcccg ggagggttcg aaaataactt ctctgttgca     120
aacccggaca aaaggcatc atggatagat tgtatatact tcggagtaac gacacactct     180
actgtcggat tcggagatat actgccaaag acgaccggcg caaagctttg tacgatagca     240
catatagtaa cagtgttctt catcgttcta actttatga                            279
```

```
<210> SEQ ID NO 3
<211> LENGTH: 234
<212> TYPE: PRT
<213> ORGANISM: Artificial Sequence
<220> FEATURE:
<223> OTHER INFORMATION: BLINK1

<400> SEQUENCE: 3

Met Gly Cys Thr Val Ser Ala Glu Leu Ala Thr Thr Leu Glu Arg Ile
1               5                   10                  15

Glu Lys Asn Phe Val Ile Thr Asp Pro Arg Leu Pro Asp Asn Pro Ile
            20                  25                  30

Ile Phe Ala Ser Asp Ser Phe Leu Gln Leu Thr Glu Tyr Ser Arg Glu
        35                  40                  45

Glu Ile Leu Gly Arg Asn Cys Arg Phe Leu Gln Gly Pro Glu Thr Asp
    50                  55                  60

Arg Ala Thr Val Arg Lys Ile Arg Asp Ala Ile Asp Asn Gln Thr Glu
65                  70                  75                  80

Val Thr Val Gln Leu Ile Asn Tyr Thr Lys Ser Gly Lys Lys Phe Trp
                85                  90                  95

Asn Leu Phe His Leu Gln Pro Met Arg Asp Gln Lys Gly Asp Val Gln
            100                 105                 110

Tyr Phe Ile Gly Val Gln Leu Asp Gly Thr Glu His Val Arg Asp Ala
        115                 120                 125

Ala Glu Arg Glu Gly Val Met Leu Ile Lys Lys Thr Ala Glu Val Phe
    130                 135                 140

Ser Lys Phe Leu Thr Arg Thr Glu Pro Phe Met Ile His Leu Phe Ile
145                 150                 155                 160

Leu Ala Met Phe Val Met Ile Tyr Lys Phe Phe Pro Gly Gly Phe Glu
                165                 170                 175

Asn Asn Phe Ser Val Ala Asn Pro Asp Lys Lys Ala Ser Trp Ile Asp
            180                 185                 190

Cys Ile Tyr Phe Gly Val Thr Thr His Ser Thr Val Gly Phe Gly Asp
        195                 200                 205

Ile Leu Pro Lys Thr Thr Gly Ala Lys Leu Cys Thr Ile Ala His Ile
    210                 215                 220

Val Thr Val Phe Phe Ile Val Leu Thr Leu
225                 230
```

```
<210> SEQ ID NO 4
<211> LENGTH: 705
<212> TYPE: DNA
<213> ORGANISM: Artificial Sequence
<220> FEATURE:
<223> OTHER INFORMATION: BLINK1

<400> SEQUENCE: 4
atgggatgta cagtctctgc agagttggct actacacttg aacgtattga gaagaacttt      60
gtcattactg acccaaggtt gccagataat cccattatat tcgcgtccga tagtttcttg     120
```

```
cagttgacag aatatagccg tgaagaaatt tgggaagaa actgcaggtt tctacaaggt      180
cctgaaactg atcgcgcgac agtgagaaaa attagagatg ccatagataa ccaaacagag      240
gtcactgttc agctgattaa ttatacaaag agtggtaaaa agttctggaa cctctttcac      300
ttgcagccta tgcgagatca gaagggagat gtccagtact ttattggggt tcagttggat      360
ggaactgagc atgtccgaga tgctgccgag agagagggag tcatgctgat taagaaaact      420
gcagaagtgt ttagtaaatt tctaacgcga actgaaccat tcatgataca tctctttatt      480
ctcgcaatgt tcgtgatgat ctataaattc ttcccgggag ggttcgaaaa taacttctct      540
gttgcaaacc cggacaaaaa ggcatcatgg atagattgta tatacttcgg agtaacgaca      600
cactctactg tcggattcgg agatatactg ccaaagacga ccggcgcaaa gctttgtacg      660
atagcacata tagtaacagt gttcttcatc gttctaactt tatga                      705

<210> SEQ ID NO 5
<211> LENGTH: 1310
<212> TYPE: DNA
<213> ORGANISM: Artificial Sequence
<220> FEATURE:
<223> OTHER INFORMATION: Myb60_TAIR10

<400> SEQUENCE: 5
cacaaggaca caaggacata tggtatgatg atatgctttg tttctctgct tctcttacta       60
atttgaagct gttggattga tttgtctctt cttacgttcc cttcttttt ttttcgtttt       120 cttttgtcgt atagaccagg caggggctag ggcctagtga tgggtattgg cccaatacta      180
ttgggttatt tgcctggttt attatttcga ttttaggtta attcaatttt aagaatacgt      240
agatttgttt ggtttagttt ggtttggttg cactaagttc ggttttacat aaatagaatc      300
taacactact aattgttata cgtaaaatac aacaacaata acagattttt cgtttcaatt      360
ttcgtttaag agggtagaca ttttggtttg gtttggttca tttttttttt ccctttcaaa      420
ttcacatcct tcacgtagat gacaaaataa agaaaaacat gaatgaaagt tgtaacttgt      480
aagcatcaac atggaaatca tatcacaaag aacacaaatc taactaatgg gtcttttcac      540
atattggtat aattataagt tgtaagaata ttagttaaac agaggcaacg agagatgcgt      600
gatatatgaa aagttgaaaa caaaagacat ggatctaaag agtcaagcaa aatgtaatat      660 cttttttttct tctaaacttg aggatgtcca agttgcagtg aatgattccc tttaatcatg      720
gagaaattca atgaaataat tgtgtttctt cccacacttt atctttattt attttcttac      780
cacaattaca actattatca caaaaatgta agtaacatag cttgtgactc ttcttccatt      840
tatgagttga ttatcactat atttataagt aattaccaac gaatgttcca aattaagcaa      900
aatattgtaa tcgatacact atgtattcat ctacaatatg ttaacgagct ccttttatgg      960
aaatatttcg attgaaaaaa catttgatgg atcgttcact aaataaataa tccagtaacg     1020
ttttcttaag ggagatatac atattcgtgt ggagatcaac atatcttcgt taattgacta     1080
cgcaaaatag ttaatggaaa aggcagagtg actcgtgagc ttggcagatc caaaagaggt     1140
tgtcaagaaa aagcagattt aaaagttctt ccctcttctt taagtcaccc attaatttca     1200
catatatgta catacatgtt gcatttaact catatacata catattctca catctataaa     1260
gagagcataa gactcagaga gatctagagg aagagagaga gagaaagatg               1310

<210> SEQ ID NO 6
<211> LENGTH: 1327
<212> TYPE: DNA
```

<213> ORGANISM: Artificial Sequence
<220> FEATURE:
<223> OTHER INFORMATION: Myb60 used for BLINK1

<400> SEQUENCE: 6

```
cacaaggaca caaggacata tggtatgatg atatgctttg tttctctgct tctcttacta    60
atttgaagct gttggattga tttgtctctt cttacgtccc cttctttttt ttttcgtttt   120
cttttgtcgc atagaccagg caggggctag ggcctagtga tgggtattgg cccaatacta   180
ttgggttatt tgcctggttt attatttcga ttttaggtta attcaatttt aagaatacgt   240
agatttgttt ggtttagttt ggtttggttg cactaagttc ggttttacat aaatagaatc   300
taacactact aattgttata cgtaaaatac aacaacaata acagattttt cgtttcaatt   360
ttcgtttaag agggtagaca ttttggtttg gtttggttca ttttttttt cccttttcaaa   420
ttcacatcct tcacgtagat gacaaaataa agaaaaacat gaatgaaagt tgtaacttgt   480
aagcatcaac atggaaatca tatcacaaag aacacaaatc taactaatgg gcctttcac    540
atattggtat aattataagc tgtaagaata ttagttaaac agaggcaacg agagatgcgt   600
gatatatgaa aagttgaaaa caaaagacat ggatctaaag agtcaagcaa aatgtaatat   660
cttttttttct tctaaacttg aggatgtcca agttgcagtg aatgattccc tttaatcatg   720
gagaaattca atgaaataat tgtgtttctt cccacacttt atctttattt attttcttac   780
cacaattaca actattatca caaaaatgaa agtaacatag cttgtgactc ttcttccatt   840
tatgagttga ttatcactat atttataagt aattaccaac gaatgttcca aattaagcaa   900
aatattgtaa tcgatacact atgtattcat ctacaatatg ttaacgagct ccttttatgg   960
aaatatttcg attgaaaaaa catttgatgg atcgttcact aaataaataa tccagtaacg  1020
ttttcttaag ggagatatac atattcgtgt ggagatcaac atatcttcgt taattgacta  1080
cgcaaaatag ttaatggaaa aggcagagtg actcgtgagc ttggcagatc caaaagaggt  1140
tgtcaagaaa aagcagattt aaaagttctt ccctcttctt taagtcaccc attaatttca  1200
catatatgta catacatgtt gcatttaact catatacata catattctca catctataaa  1260
gagagcataa gactcagaga gatctagaac tagtgatatc acaagtttgt acaaaaaagc  1320
aggctta                                                            1327
```

<210> SEQ ID NO 7
<211> LENGTH: 1728
<212> TYPE: DNA
<213> ORGANISM: Artificial Sequence
<220> FEATURE:
<223> OTHER INFORMATION: GC1

<400> SEQUENCE: 7

```
cttctacaag aagagtaaag attcagtaac ccgatgctcc tgctcttcct caagaccttc    60
cttgattcgc cgccggtatg ttctccgtct gtggtagcgc ctttggaaca ctctaccaac   120
gccgccatga aaggatctct catggccgca ggggacgtgt tcttcttaca tctggtgtta   180
gggctatggt tactccagtg aggagggaga ggcaagaggt tgcttaatga ttcgtttttc   240
cggtgatacg agaactcttt aggtttaccg ggaagctttt cccatgaaaa tgggatgcca   300
agtggatgga gaggagttgc cggagagttg ccggagaata ggagggaatt ggaggaggag   360
gaagagagtg atcgccgggt tgaaatgtta accgtcgagg agaatttgac cgagttggat   420
cgtctagtag gtacaattcg ggtccttggc gaagtatcca ttcaaaatag tgtttagttt   480
tggacttgag aacttgttgt ctctttgatc tcttttatat aaaactttgg acgtgtagga   540
```

-continued

```
caaacttgtc aacataagaa acaaaatggt tgcaacagag aggatgaatt tataagtttt      600
caacaccgct tttcttatta gacggacaac aatctatagt ggagtaaatt tttatttttg      660
gtaaaatggt tagtgaattc aaatatctaa attttgtgac tcactaacat taacaaatat      720
gcataagaca taaaaaaaag aaagaataat tcttatgaaa caagaaaaaa aacctataca      780
atcaatcttt aggaattgac gatgtagaat tgtagatgat aaattttctc aaatatagat      840
gggcctaatg aagggtgccg cttattggat ctgacccatt ttgaggacat taatattttc      900
attggttata agccttttaa tcaaaattgt cattaaattg atgtctccct ctcgggtcat      960
tttccttcct ccctcacaat taatgtgac tttagcaatt tgcacgctgt gctttgtctt      1020
tatatttagt aacacaaaca ttttgacttg tcttgtagag ttttctctt ttattttct       1080
atccaatatg aaaactaaaa gtgttctcgt atacatatat taaaattaaa gaaacctatg      1140
aaaacaccaa tacaaatgcg atattgtttt cagttcgacg tttcatgttt gttagaaaat      1200
ttctaatgac gtttgtataa aatagacaat taaacgccaa acactacatc tgtgttttcg      1260
aacaatattg cgtctgcgtt tccttcatct atctctctca gtgtcacaat gtctgaacta      1320
agagacagct gtaaactatc attaagacat aaactaccaa agtatcaagc taatgtaaaa      1380
attactctca tttccacgta acaaattgag ttagcttaag atattagtga aactaggttt      1440
gaattttctt cttcttcttc catgcatcct ccgaaaaaag ggaaccaatc aaaactgttt      1500
gcatatcaaa ctccaacact ttacagcaaa tgcaatctat aatctgtgat ttatccaata      1560
aaaacctgtg atttatgttt ggctccagcg atgaaagtct atgcatgtga tctctatcca      1620
acatgagtaa ttgttcagaa aataaaaagt agctgaaatg tatctatata aagaatcatc      1680
cacaagtact attttcacac actacttcaa aatcactact caagaaat                  1728
```

<210> SEQ ID NO 8
<211> LENGTH: 258
<212> TYPE: PRT
<213> ORGANISM: Artificial Sequence
<220> FEATURE:
<223> OTHER INFORMATION: BLINK 1 variant (myLK)

<400> SEQUENCE: 8

```
Met Gly Cys Thr Val Ser Ala Glu Leu Ala Thr Thr Leu Glu Arg Ile
1               5                   10                  15

Glu Lys Asn Phe Val Ile Thr Asp Pro Arg Leu Pro Asp Asn Pro Ile
            20                  25                  30

Ile Phe Ala Ser Asp Ser Phe Leu Gln Leu Thr Glu Tyr Ser Arg Glu
        35                  40                  45

Glu Ile Leu Gly Arg Asn Cys Arg Phe Leu Gln Gly Pro Glu Thr Asp
    50                  55                  60

Arg Ala Thr Val Arg Lys Ile Arg Asp Ala Ile Asp Asn Gln Thr Glu
65                  70                  75                  80

Val Thr Val Gln Leu Ile Asn Tyr Thr Lys Ser Gly Lys Lys Phe Trp
                85                  90                  95

Asn Leu Phe His Leu Gln Pro Met Arg Asp Gln Lys Gly Asp Val Gln
            100                 105                 110

Tyr Phe Ile Gly Val Gln Leu Asp Gly Thr Glu His Val Arg Asp Ala
        115                 120                 125

Ala Glu Arg Glu Gly Val Met Leu Ile Lys Lys Thr Ala Glu Asn Ile
    130                 135                 140

Asp Glu Ala Ala Lys Glu Leu Pro Asp Ala Asn Leu Arg Pro Glu Asp
```

```
                    145                 150                 155                 160
Leu Trp Ala Asn His Ser Val Phe Ser Lys Phe Leu Thr Arg Thr Glu
                165                 170                 175

Pro Phe Met Ile His Leu Phe Ile Leu Ala Met Phe Val Met Ile Tyr
            180                 185                 190

Lys Phe Pro Gly Gly Phe Glu Asn Asn Phe Ser Val Ala Asn Pro
        195                 200                 205

Asp Lys Lys Ala Ser Trp Ile Asp Cys Ile Tyr Phe Gly Val Thr Thr
    210                 215                 220

His Ser Thr Val Gly Phe Gly Asp Ile Leu Pro Lys Thr Thr Gly Ala
225                 230                 235                 240

Lys Leu Cys Thr Ile Ala His Ile Val Thr Val Phe Phe Ile Val Leu
                245                 250                 255

Thr Leu

<210> SEQ ID NO 9
<211> LENGTH: 777
<212> TYPE: DNA
<213> ORGANISM: Artificial Sequence
<220> FEATURE:
<223> OTHER INFORMATION: BLINK 1 variant (myLK)

<400> SEQUENCE: 9
atgggatgta cagtctctgc agagttggct actacacttg aacgtattga gaagaacttt      60
gtcattactg acccaaggtt gccagataat cccattatat tcgcgtccga tagtttcttg     120
cagttgacag aatatagccg tgaagaaatt ttgggaagaa actgcaggtt tctacaaggt     180
cctgaaactg atcgcgcgac agtgagaaaa attagagatg ccatagataa ccaaacagag     240
gtcactgttc agctgattaa ttatacaaag agtggtaaaa agttctggaa cctcttttcac    300 ttgcagccta tgcgagatca gaagggagat gtccagtact ttattggggt tcagttggat     360
ggaactgagc atgtccgaga tgctgccgag agagagggag tcatgctgat taagaaaact     420
gcagaaaata ttgatgaggc ggcaaaagaa cttccagatg ctaatttgag accagaggat     480
ttgtgggcta accactcagt gtttagtaaa tttctaacgc gaactgaacc attcatgata     540
catctcttta ttctcgcaat gttcgtgatg atctataaat tcttcccggg agggttcgaa     600
aataacttct ctgttgcaaa cccggacaaa aaggcatcat ggatagattg tatatacttc     660
ggagtaacga cacactctac tgtcggattc ggagatatac tgccaaagac gaccggcgca     720
aagctttgta cgatagcaca tatagtaaca gtgttcttca tcgttctaac tttatga        777

<210> SEQ ID NO 10
<211> LENGTH: 820
<212> TYPE: PRT
<213> ORGANISM: Artificial Sequence
<220> FEATURE:
<223> OTHER INFORMATION: GORK

<400> SEQUENCE: 10

Met Gly Arg Leu Arg Arg Arg Gln Glu Ile Ile Asp His Glu Glu Glu
1               5                   10                  15

Glu Ser Asn Asp Asp Val Ser Ser Arg Arg Gly Lys Leu Ser Leu Ala
            20                  25                  30

Glu Thr Phe Arg Trp Leu Asp Ser Ser Glu His Arg Arg Ile Glu Thr
        35                  40                  45

Asp Gly His Asn Asp Tyr Lys Tyr Ile Ile His Pro Lys Asn Arg Trp
    50                  55                  60
```

```
Tyr Lys Ala Trp Glu Met Phe Ile Leu Val Trp Ala Ile Tyr Ser Ser
 65                  70                  75                  80

Leu Phe Thr Pro Met Glu Phe Gly Phe Arg Gly Leu Pro Glu Arg
             85                  90                  95

Leu Phe Val Leu Asp Ile Val Gly Gln Ile Ala Phe Leu Val Asp Ile
                100                 105                 110

Val Leu Gln Phe Phe Val Ala Tyr Arg Asp Thr Gln Thr Tyr Arg Thr
            115                 120                 125

Val Tyr Lys Pro Thr Arg Ile Ala Phe Arg Tyr Leu Lys Ser His Phe
            130                 135                 140

Leu Met Asp Phe Ile Gly Cys Phe Pro Trp Asp Leu Ile Tyr Lys Ala
145                 150                 155                 160

Ser Gly Lys His Glu Leu Val Arg Tyr Leu Leu Trp Ile Arg Leu Phe
                165                 170                 175

Arg Val Arg Lys Val Val Glu Phe Phe Gln Arg Leu Glu Lys Asp Thr
            180                 185                 190

Arg Ile Asn Tyr Leu Phe Thr Arg Ile Leu Lys Leu Leu Phe Val Glu
            195                 200                 205

Val Tyr Cys Thr His Thr Ala Ala Cys Ile Phe Tyr Tyr Leu Ala Thr
210                 215                 220

Thr Leu Pro Pro Glu Asn Glu Gly Tyr Thr Trp Ile Gly Ser Leu Lys
225                 230                 235                 240

Leu Gly Asp Tyr Ser Tyr Glu Asn Phe Arg Glu Ile Asp Leu Trp Lys
                245                 250                 255

Arg Tyr Thr Thr Ala Leu Tyr Phe Ala Ile Val Thr Met Ala Thr Val
            260                 265                 270

Gly Tyr Gly Asp Ile His Ala Val Asn Leu Arg Glu Met Ile Phe Val
            275                 280                 285

Met Ile Tyr Val Ser Phe Asp Met Val Leu Gly Ala Tyr Leu Ile Gly
    290                 295                 300

Asn Ile Thr Ala Leu Ile Val Lys Gly Ser Asn Thr Glu Arg Phe Arg
305                 310                 315                 320

Asp Lys Met Asn Asp Leu Ile Ser Phe Met Asn Arg Lys Lys Leu Gly
                325                 330                 335

Arg Asp Leu Arg Ser Gln Ile Thr Gly His Val Arg Leu Gln Tyr Asp
            340                 345                 350

Ser His Tyr Thr Asp Thr Val Met Leu Gln Asp Ile Pro Ala Ser Ile
            355                 360                 365

Arg Ala Lys Ile Ala Gln Leu Leu Tyr Leu Pro Tyr Ile Lys Lys Val
            370                 375                 380

Pro Leu Phe Lys Gly Cys Ser Thr Glu Phe Ile Asn Gln Ile Val Ile
385                 390                 395                 400

Arg Leu His Glu Glu Tyr Phe Leu Pro Gly Glu Val Ile Thr Glu Gln
                405                 410                 415

Gly Asn Val Val Asp His Leu Tyr Phe Val Cys Glu Gly Leu Leu Glu
            420                 425                 430

Ala Leu Val Thr Lys Thr Asp Gly Ser Glu Glu Ser Val Thr Leu Leu
            435                 440                 445

Gly Pro His Thr Ser Phe Gly Asp Ile Ser Ile Ile Cys Asn Ile Ser
            450                 455                 460

Gln Pro Phe Thr Val Arg Val Cys Glu Leu Cys His Leu Leu Arg Leu
465                 470                 475                 480
```

Asp Lys Gln Ser Phe Ser Asn Ile Leu Glu Ile Tyr Phe His Asp Gly
            485                 490                 495

Arg Thr Ile Leu Asn Asn Ile Met Glu Glu Lys Glu Ser Asn Asp Arg
        500                 505                 510

Ile Lys Lys Leu Glu Ser Asp Ile Val Ile His Ile Gly Lys Gln Glu
        515                 520                 525

Ala Glu Leu Ala Leu Lys Val Asn Ser Ala Ala Phe Gln Gly Asp Phe
    530                 535                 540

Tyr Gln Leu Lys Ser Leu Ile Arg Ser Gly Ala Asp Pro Asn Lys Thr
545                 550                 555                 560

Asp Tyr Asp Gly Arg Ser Pro Leu His Leu Ala Ala Cys Arg Gly Tyr
                565                 570                 575

Glu Asp Ile Thr Leu Phe Leu Ile Gln Glu Gly Val Asp Val Asn Leu
            580                 585                 590

Lys Asp Lys Phe Gly His Thr Pro Leu Phe Glu Ala Val Lys Ala Gly
        595                 600                 605

Gln Glu Gly Val Ile Gly Leu Leu Val Lys Glu Gly Ala Ser Phe Asn
    610                 615                 620

Leu Glu Asp Ser Gly Asn Phe Leu Cys Thr Thr Val Ala Lys Gly Asp
625                 630                 635                 640

Ser Asp Phe Leu Lys Arg Leu Leu Ser Ser Gly Met Asn Pro Asn Ser
                645                 650                 655

Glu Asp Tyr Asp His Arg Thr Pro Leu His Val Ala Ala Ser Glu Gly
            660                 665                 670

Leu Phe Leu Met Ala Lys Met Leu Val Glu Ala Gly Ala Ser Val Ile
        675                 680                 685

Ser Lys Asp Arg Trp Gly Asn Ser Pro Leu Asp Glu Ala Arg Leu Cys
    690                 695                 700

Gly Asn Lys Lys Leu Ile Lys Leu Leu Glu Asp Val Lys Asn Ala Gln
705                 710                 715                 720

Ser Ser Ile Tyr Pro Ser Ser Leu Arg Glu Leu Gln Glu Glu Arg Ile
                725                 730                 735

Glu Arg Arg Lys Cys Thr Val Phe Pro Phe His Pro Gln Glu Ala Lys
            740                 745                 750

Glu Glu Arg Ser Arg Lys His Gly Val Val Val Trp Ile Pro Ser Asn
        755                 760                 765

Leu Glu Lys Leu Ile Val Thr Ala Ala Lys Glu Leu Gly Leu Ser Asp
    770                 775                 780

Gly Ala Ser Phe Val Leu Leu Ser Glu Asp Gln Gly Arg Ile Thr Asp
785                 790                 795                 800

Ile Asp Met Ile Ser Asp Gly His Lys Leu Tyr Met Ile Ser Asp Thr
                805                 810                 815

Thr Asp Gln Thr
            820

<210> SEQ ID NO 11
<211> LENGTH: 5542
<212> TYPE: DNA
<213> ORGANISM: Artificial Sequence
<220> FEATURE:
<223> OTHER INFORMATION: GORK

<400> SEQUENCE: 11
ctagacaaaa ccttacgtta tacacttcaa ctaataaaga gtccaaacca aacaaaaaaa      60
aaacagtagt ttctcgacag aaacaaaatc aatatagctt taacatcacg agaaagaaga    120

```
actaagaag accaaacaaa aaataatttg gaaaaaaaca gagaagcagc tctcgtgatc      180
ttcccgcctt ttctcttcaa cttgtaaaac attacaagat ctatcttcta ccaaaaagac      240
gaagtttcga gtgtcagatt caagagttga atcgggtatt aaactctgtt tttctagatc      300
tttgtgtcga agagatcgcc ggagatttca tttaaccgat tcttgaaaac atgggacgtc      360
tccggagacg gcaagagata atagatcatg aagaagagga atcaaacgac gacgtttcat      420
caagaagagg aaaactcagt ttagccgaga cgtttcggtg gcttgattca tcagagcatc      480
ggagaattga aaccgatggt cataatgatt ataaatacat cattcatccc aaaaacaggt      540
tctttctttt ttctctttct tcatcatgca cttgaagagt ttccttcta tcgggagata       600 aatacgtaga aaatactttt cttgaaacct tcaaatatc ttctgttttt ttttctgtaa       660
cttcagaaaa aaactttatt caccatacca cttcaaaaac ttgtctccct agttttaact      720
tcgaataata caataataga aaattcacca ttttaataat tatcaatcac taaaactctt      780
atcgttattt cttctgctc attttttaagg ctgtgtcacc aatctaatct aatattagta      840
tcacttcaat ctagtttaaa tattaatatt tatgtcaagg attttttaaa caactaaat       900 gatttaaggt tcgaaaaatt acgataatta gaatggacaa atccgtttac agtttggatt      960
gctttttatt taccgttcat aaagtataat ttatagtaat acaaataat aaaaatagaa      1020 tccgtctaca atggactaac gatatatctt ttttacgtaa aagtgaattt ggtctacaga     1080
atttattgtt cgctctaaaa ataaaatggt ctaatcgctt aattcgtatc atccattaat     1140
agccttagga tttagatgaa taatcttcat cacttatcaa aagtagatat tagatgctaa     1200
tcaggtgatt ttgttgtcga tattcttttc attattattt actaagaaaa aagaaattgg     1260
tgggacactt ccttgtgata tatttcttct ctttcgttgt ccactgatca cctcaatcta     1320
agcatttgtt ttatttgcag ccgacctatt gaaaatttaa aacttaaatc taaaaccaaa     1380
ttccgaccaa aacaaggaaa aactttaaat ctatctttaa atagaatcct acgttaaatt     1440
gcaccaggaa taaaaaaaaa aatactacgt taaacaactt gaatccacta gaggatactg     1500
ttacactccc ataaatgttt cactagggtt atattagtaa ttatgcgttg tgacagaatc     1560
atcgaagatc ggattattaa ttggttccac taaagctgcc gtaaccagag ccacacgtg      1620 gatatttcat ccacctgttc ttctaagcat aataacatta actataaaat aacaaaacta     1680
tactagtgaa aatgtatatt caacttagtc cagctatgtc gatcttaaac aaataaaatt     1740
taaaacgttg ttgcttgcac ttaactaata actatagtat tattttcatt tgtctccttc     1800
ccacgattcc gtttagctac attaccaatt tgacgaatca agtataagcc acaatcttta     1860
cattttcaag aatctttgat tagacctgaa ttaatgaaaa gtgagaagaa attgatcagg     1920
tggtacaagg catgggaaat gtttatattg gtgtgggcaa tatactcctc attgttcact     1980
cccatggagt ttggtttctt ccgcggtctg cctgagagac tctttgtact tgacattgtt     2040
ggtcagatcg cgttcttggt cgatattgtt cttcagttct tgttgccta tcgcgatact     2100 cagacctacc ggactgtcta caaaccaaca cgtattgctt tccggtcagt tatatatatt     2160
agactcttac aatcatttta accatttcta cttatatagc ctttaatgga ggaagtatgt     2220
ctttcatcag gtacttgaag tcgcatttttc tcatggattt catcggttgc ttcccttggg     2280 atcttatttta taaggtactt aactttgctt ttgatatttg cttagatctt caacaaaagt     2340
caaaccaaag aaaacactata gcttataaat atttcttggt ttataaaaac tcaaaccaaa     2400
taaacactat ttgtaatttg tttggttcgt ttctaggtga tgcaacttta gttcctactt     2460
```

```
gatgcaattt tagcttagtt aggttggaaa ttttgtaaaa gtaactttga aacatataaa    2520
aatatttctt aactaatatt atatttatct aatatgataa cacatattat aatttcttat    2580
ataattaaaa taaaattcac ataaatatca attcatttgg ttagtttaca ctaaaatcag    2640
tttcacttcg atttcgatgt ttaaataata aaccaattgg gttatttaaa tacatttttg    2700
gttctgattc ggtttggttt ggtttatact cctaccctaa cctttttgta ggcatcaggg    2760
aaacatgagt tggtgaggta cttgttgtgg ataaggctat ttcgggttcg caaagtggtt    2820 gagttttttcc aaaggcttga gaaagacaca agaatcaact atctattcac tagaatctta    2880
aagctcttgt tcgttgaagt ttattgtact cacactgctg cttgtatctt ctattacttg    2940
gccaccactc ttcctccaga aaacgaaggt tacacttgga tcggtagctt gaagctagga    3000
gactatagct acgagaattt ccgagaaatc gatctctgga aacgttatac taccgctcta    3060
tacttcgcca ttgtcactat ggcaactgtc ggtataaaaa ccaattctat tttgatgcta    3120
atttaattag ttactaacaa agagattgat gggtttttttt tttttcgttt tggttttagg    3180
ttatggagac attcacgcgg tgaatctgag ggaaatgata ttcgtgatga tatatgtttc    3240
gtttgatatg gttctcggtg cttaccttat tggtaacatc actgccttga ttgtgaaagg    3300
ttcaaacaca gagaggttca gagataaaat gaatgatctc ataagtttca tgaaccgcaa    3360
aaaactcggg agagaccttc gtagccagat aactggtcat gttagattgc agtacgacag    3420
tcactacacc gacactgtca tgcttcagga catcccagca tcaatccgcg ccaaggtacc    3480
ctaattataa aaacaaaatt ctcgttttgt taccaacaaa tattcatgta cttttttaggt    3540 tagagttagt gtttcttgga acacaatctt tgtcaagccg gtccgcataa cccgctcaat    3600
atcttagcct gctgcatgac ggattagcgc gcattgacac cctaactaat acacattttt    3660
cttgcagatt gcgcaattat tgtatctgcc ttacatcaaa aaagttcctc tcttcaaagg    3720
ctgctccaca gagtttatta atcaaatagt tataaggctc catgaagagt attttcttcc    3780
aggagaagta ataacagagc aaggaaacgt cgtggatcat ttgtatttcg tctgtgaagg    3840
cttactggta cgtaaaatct cattgtgctt gtgtctatct ttgcttcttg tatgtctcac    3900
tttgtaattt ttggggatttt ttataggagg ctcttgttac aaaaacagat ggatcagaag    3960
agagtgtgac gttacttggg cctcacactt cttttggaga catctccatc atttgcaaca    4020
tttctcaacc tttcactgtt agggtttgtg agctatgcca tcttttacga ctcgataaac    4080
agtctttctc aaacatcctc gagatttatt ttcacgacgg acgcacaatc ttgaacaata    4140
ttatggaggt actctttttt ctatctctta cttagggttt tgaaactcga ttgagaaatc    4200
ttgcaactca ctcaaacttg gttttggcag gagaaggaat caaatgatag gataaagaag    4260
ctagaatctg acatagtgat tcacattggg aaacaagaag cagaacttgc attgaaagta    4320
aacagtgcag ctttccaagg agatttttac cagcttaaga gcttaatccg atctggagcc    4380
gatcctaaca aaaccgatta cgatggaaga tcaccgcttg tacgtttgtc gcttatcgat    4440
tatctttctt ttaagagctt aactttgatt ctttttttata tccagcatct tgcagcatgt    4500
agaggctatg aagacattac attattcctt attcaggaag gtgttgatgt caatctaaaa    4560
ggtaaaatat gaatcgttct aatggaaaac attacattgt tttatgttta cgcttttgat    4620
cacaaatttt cgcagataag ttcggacaca caccattgtt tgaggctgtg aaagcaggac    4680
aagaaggagt gattggtttg cttgtcaaag aaggagcctc ctttaattta gaagattcag    4740
gaaacttcct ttgcacgaca gttgctaaag gcgactctga ttttctcaag agattgcttt    4800
caagcggtat gaacccaaac agtgaagatt atgatcacag aacgccgctt catgtcgcgg    4860
```

```
cttctgaagg gttattcttg atggctaaaa tgttggttga agctggagca agcgttattt   4920
ctaaagaccg gtaaaaatca tgcaaaatga atcatttaat tctttaaaac tatagtttat   4980
agacttcata acttctctct ttgaagatgg gggaattctc cgcttgatga agcccgattg   5040
tgcggaaaca agaaactgat taagttactc gaagatgtga aaaatgctca gtcgtctatc   5100
tacccgtcaa gcttgcgtga attacaaggt actcgtatac ttccttcaga cgatacaact   5160
caaaaatgga tcttgtaatt cttgaatttg atttatgttt tgaaaaacag aggagagaat   5220
tgagagacgg aaatgcacgg tgtttccatt ccacccgcaa gaggcgaaag aagagcgtag   5280
tagaaagcac ggagttgtgg tttggatccc aagcaatctc gagaaactca tagtaaccgc   5340
tgcgaaagag ctagggctat cggatggagc ctcatttgta ctattatcag aagaccaagg   5400
tcgtatcaca gacattgata tgattagtga tggacacaaa ttgtatatga tcagtgatac   5460
tactgatcaa acataatgat ggactcttcg atttttccga tgattcattt gaggttttta   5520
tattctagag cattttgaca ca                                            5542
```

<210> SEQ ID NO 12
<211> LENGTH: 1949
<212> TYPE: DNA
<213> ORGANISM: Artificial Sequence
<220> FEATURE:
<223> OTHER INFORMATION: CER6 Promoter

<400> SEQUENCE: 12

```
tagtgcttta tatatgtttg atacttctgt ttggcaatat caatcatagt agaaaagata     60
tggacttcat ttgaggtttt tggtggattg tgtctatatg tgaaatcatg ggatctcaag    120
atttgtctgc attcagtttc caagtcaaac atcgtaacta ctgtttgatt ttccctcatg    180
cttgcagttt tcatggatat ctcaagattt gtcttcttgc actttccaag tcaaacataa    240
agtaactact gattgatatt ccctcgtgta ttaccctctt tcaaatgaca caattgggcc    300
caagtagagg aatttcatag tgaattcaaa agattaactg tattccaccg tcgtattttg    360
ataacattta gttattcctt ttcttttttt tcttctgcaa cagttttttt ttaatacatt    420
tagtgttggt ttggttcaat gaaatattat atgttacttc ttttttggaa aataaattat    480
tcattctttc tactataaaa ggaattgttc atgcttttt gatacaatag tataccattt     540
caaaagatac catagaccag ttattacatg aatcgccaaa acaacactaa aatcagaaaa    600
tcagtatatt ttggtatagt ctccaacata caatcataaa acctctgtga aatttaaaat    660
ctatatttga catttcaaag tttaacaaca tagttctaaa taattaccta aatttaagtc    720
aaatgtgaat tatatttact cttcgatatc ggttgttgac gattaaccat gcaaaaaga    780 aacattaatt gcgaatgtaa ataacaaaac atgtaactct tgtagatata catgtatcga    840
catttaaacc cgaatatata tgtataccta taatttctct gattttcacg ctacctgcca    900
cgtacatggg tgataggtcc aaactcacaa gtaaagtttt acgtacagtg aattcgtctt    960
tttgggtata aacgtacatt taatttacac gtaagaaagg attaccaatt ctttcattta   1020
tggtaccaga cagagttaag gcaaacaaga gaaacatata gagttttgat atgttttctt   1080
ggataaatat taaattgatg caatatttag ggatggacac aaggtaatat atgcctttta   1140
aggtatatgt gctatatgaa tcgtttcgca tgggtactaa aattatttgt ccttacttta   1200
tataaacaaa ttccaacaaa atcaagtttt tgctaaaact agttatttgc gggttattta   1260
attacctatc atattacttg taatatcatt cgtatgttaa cgggtaaacc aaaccaaacc   1320
```

```
ggatattgaa ctattaaaaa tcttgtaaat ttgacacaaa ctaatgaata tctaaattat   1380
gttactgcta tgataacgac cattttttgtt tttgagaacc ataatataaa ttacaggtac   1440
gtgacaagta ctaagtattt atatccacct ttagtcacag taccaatatt gcgcctaccg   1500
ggcaacgtga acgtgatcat caaatcaaag tagttaccaa acgctttgat ctcgataaaa   1560
ctaaaagctg acacgtcttg ctgtttctta atttatttct cttacaacga caattttgag   1620
aaatatgaaa ttttttatatc gaaagggaac agtccttatc atttgctccc atcattgctt   1680
ttgtctagtt acaactggaa atcgaagaga agtattacaa aaacattttt ctcgtcattt   1740
ataaaaaaat gacaaaaaat taaatagaga gcaaagcaag agcgttgggt gacgttggtc   1800
tcttcattaa ctcctctcat ctacccctttc ctctgttcgc ctttatatcc ttcaccttcc   1860
ctctctcatc ttcattaact atcttcaaaa atacccctaat cacattttgt aacaataata   1920
caattataca ttaaaactct ccgacgatg                                       1949

<210> SEQ ID NO 13
<211> LENGTH: 2198
<212> TYPE: DNA
<213> ORGANISM: Artificial Sequence
<220> FEATURE:
<223> OTHER INFORMATION: TaGSTA1 promoter

<400> SEQUENCE: 13
tgggaggagg ccttggatgt tgatctccat ttatacacag agcagggagc accacacccg     60
gcccgcgtgg cccaaggaaa taacaaggct acatcgactt tttagctagt gtctagatct    120
gctttatttc atttctacca aaaagatat atgaaatgat gagtgccaaa ttaaatgagc    180
tcttgaatca tttaaaccgg gtaagtaatc atctttgtta gtttatcgat actccctcta    240
ttccatattg tggtgcgaag gaagtaagta ctagttagaa acacgtgcgt tggtacggat    300
tggagaaaca actactccct ccattcactt ttgtagatcg cggaaccaat ttccgacagc    360
cccccaaaca tcggtgaagg accaatatac cccagataga tagatttgaa attcaaatta    420
ctccacatcg atcgcgccct tcctcccatc gtcgaggtct caatatcaga actggatcct    480
ctaacgtgga gaagggaagg caggtaagcg acagtagtca gctagtctaa atgaagaaa    540 caaagtcaga gaactgtagc aaaacactgt aaatcaactt gctactatta cgtcgctagc    600
agttggccca ttgatttagc aagtggtagg cgacatacag tgtcacttga gcaagtgtaa    660
aggtaaaaga gactttacat gcatggcggc tatccggctg ccgacatatt ccaacatgga    720 agattttttcg ctagctctac caggccacga tattccaacg cgggaagata atcgtgtccg    780
cacaacttat ttgaggcttg agagagatgg tagcaccaaa agcaatgtgc cctctcgttg    840
tctcgaaaac actaagggtg ggtatatgca tatcttatta actaaaaaag gtagaaaaat    900
gcctctaatt taaaatcaac aagtaaatgt acattccaat atgattttcg ttgtcactca    960
attgaataat ttttcactat cgatggaaat gtatttttttt ttaatctttg ttctgattca   1020
gttgaatgct ataagttccg agagttaagc ttgccagcga tcaatcattt tcccacttgc   1080
caacgccttg catgttctat aaaaaatcaa cttggatgct attattacat cgctagcagt   1140
tggcccattg gtaggcgaca catcactttt ccatggctct aaatgttcct gtttgatgct   1200
tgtgccttaa tagcaagaca gactttccac ggctctggct ctcaccagct agcgagatat   1260
ttgccaaata gttcgtttgg ctagagtgtg gaataactta ttctactctt aaacacaaag   1320
tgttaaatca ctctctccat atataactaa actacaatgt tgtataaaag atacatcgag   1380
aaggttttac gttatcccta caactttgat cctaataata atcattacat agcacaacct   1440
```

```
ttccgtaggc aaaacacctc acgaggtttg gtgttgctcc aaaagatctc tttatcaaga    1500
ctagttagta taactctttta aagttaaact aaatcatgca tgtgaagaac attcagattt    1560
actgtgcata taaatcttct aaactaaaaa aaatcacata taattttgat tgtaagcaat    1620
tatagtagat ggatatcaca catatatttt ttgcaagtta atttagatca aaataatctg    1680
aatcaggtgg atgtgaagaa ggaaagttaa agtacttagc ataccggact tgcctcctcc    1740
acgttccagg atccagttcc ctagctagca gcctagcacc tcgttgatca cgccacgccc    1800
cgttcccaga acctggccaa ttgataggcc aaatagcacc tggcctcact gatctcccca    1860
ggactcggat ctcttcgcca atcgatcggc tagcacctaa ctggcctcac cgattgtcct    1920
agcagcagca cgccggtcgg cgactcccac cccgcagcag aacgccagcc ggcgaccccc    1980
accccgcaac agaacgtcag ccggcgaccc ccacccagaa ggagcagatc gccggtgagg    2040
ggagaaggtc agcgcgtcgc catcgcccct ggttctactc gcccaacacc cgccagacca    2100
ggtgctgctc gtcatccagt cacctcgccg atccagggct agtgatctag tctgccgagg    2160
gcttgggacc tggggctgt cggctccact tcggcgtc                              2198
```

<210> SEQ ID NO 14
<211> LENGTH: 134
<212> TYPE: PRT
<213> ORGANISM: Artificial Sequence
<220> FEATURE:
<223> OTHER INFORMATION: LOV2 domain

<400> SEQUENCE: 14

```
Leu Ala Thr Thr Leu Glu Arg Ile Glu Lys Asn Phe Val Ile Thr Asp
1               5                   10                  15

Pro Arg Leu Pro Asp Asn Pro Ile Ile Phe Ala Ser Asp Ser Phe Leu
            20                  25                  30

Gln Leu Thr Glu Tyr Ser Arg Glu Glu Ile Leu Gly Arg Asn Cys Arg
        35                  40                  45

Phe Leu Gln Gly Pro Glu Thr Asp Arg Ala Thr Val Arg Lys Ile Arg
    50                  55                  60

Asp Ala Ile Asp Asn Gln Thr Glu Val Thr Val Gln Leu Ile Asn Tyr
65                  70                  75                  80

Thr Lys Ser Gly Lys Lys Phe Trp Asn Leu Phe His Leu Gln Pro Met
                85                  90                  95

Arg Asp Gln Lys Gly Asp Val Gln Tyr Phe Ile Gly Val Gln Leu Asp
            100                 105                 110

Gly Thr Glu His Val Arg Asp Ala Ala Glu Arg Glu Gly Val Met Leu
        115                 120                 125

Ile Lys Lys Thr Ala Glu
    130
```

<210> SEQ ID NO 15
<211> LENGTH: 15
<212> TYPE: PRT
<213> ORGANISM: Artificial Sequence
<220> FEATURE:
<223> OTHER INFORMATION: Jalpha helix domain

<400> SEQUENCE: 15

```
Ala Ala Glu Arg Glu Gly Val Met Leu Ile Lys Lys Thr Ala Glu
1               5                   10                  15
```

<210> SEQ ID NO 16

<211> LENGTH: 38
<212> TYPE: DNA
<213> ORGANISM: Artificial Sequence
<220> FEATURE:
<223> OTHER INFORMATION: Primer to amplify pMYB60

<400> SEQUENCE: 16
ctcactatag ggagctcaca aggacacaag gacatatg                         38

<210> SEQ ID NO 17
<211> LENGTH: 31
<212> TYPE: DNA
<213> ORGANISM: Artificial Sequence
<220> FEATURE:
<223> OTHER INFORMATION: Primer to amplify pMYB60

<400> SEQUENCE: 17
catcccatta agcctgcttt tttgtacaaa c                                31

<210> SEQ ID NO 18
<211> LENGTH: 28
<212> TYPE: DNA
<213> ORGANISM: Artificial Sequence
<220> FEATURE:
<223> OTHER INFORMATION: Primer to amplify BLINK1

<400> SEQUENCE: 18
caggcttaat gggatgtaca gtctctgc                                    28

<210> SEQ ID NO 19
<211> LENGTH: 37
<212> TYPE: DNA
<213> ORGANISM: Artificial Sequence
<220> FEATURE:
<223> OTHER INFORMATION: Primer to amplify BLINK1

<400> SEQUENCE: 19
cagcggcagc agccgtcata aagttagaac gatgaag                          37

<210> SEQ ID NO 20
<211> LENGTH: 55
<212> TYPE: DNA
<213> ORGANISM: Artificial Sequence
<220> FEATURE:
<223> OTHER INFORMATION: Primer containing attB3 site

<400> SEQUENCE: 20
ggggacaact ttgtataata aagttgtcaa catgggatgt acagtctctg cagag       55

<210> SEQ ID NO 21
<211> LENGTH: 55
<212> TYPE: DNA
<213> ORGANISM: Artificial Sequence
<220> FEATURE:
<223> OTHER INFORMATION: Primer containing AttB2 site

<400> SEQUENCE: 21
ggggaccact ttgtacaaga aagctgggta tcataaagtt agaacgatga agaac       55

<210> SEQ ID NO 22
<211> LENGTH: 20
<212> TYPE: DNA
<213> ORGANISM: Artificial Sequence
<220> FEATURE:
<223> OTHER INFORMATION: Primer to amplify BLINK

<400> SEQUENCE: 22

```
atggaactga gcatgtccga                                                    20

<210> SEQ ID NO 23
<211> LENGTH: 20
<212> TYPE: DNA
<213> ORGANISM: Artificial Sequence
<220> FEATURE:
<223> OTHER INFORMATION: Primer to amplify BLINK

<400> SEQUENCE: 23
ttttgtccgg gtttgcaaca                                                    20

<210> SEQ ID NO 24
<211> LENGTH: 23
<212> TYPE: DNA
<213> ORGANISM: Artificial Sequence
<220> FEATURE:
<223> OTHER INFORMATION: Primer to amplify ISU

<400> SEQUENCE: 24
gccatcgctt cttcatctgt tgc                                                23

<210> SEQ ID NO 25
<211> LENGTH: 24
<212> TYPE: DNA
<213> ORGANISM: Artificial Sequence
<220> FEATURE:
<223> OTHER INFORMATION: Primer to amplify ISU

<400> SEQUENCE: 25
gtggggagag aaagatgctt tgcg                                               24
```

METHODS FOR OPTOGENETIC MANIPULATION OF STOMATAL FUNCTION

FIELD OF THE INVENTION

The invention relates to methods of increasing stomatal function in plants, which leads to an increase in carbon assimilation and/or water use efficiency and ultimately an increase in yield. In particular the methods of the invention relate to the expression of light-gated potassium channels in the stomatal complex. Also described are genetically altered plants characterised by the above phenotype as well as methods of producing such plants.

BACKGROUND OF THE INVENTION

Globally, water usage has increased 6-fold in the past 100 years, twice as fast as the human population, and is expected to double again before 2030, driven mainly by irrigation and agriculture. In the UK alone, irrigation has risen 10-fold in the past 30 years and this trend is expected to continue.

Stomata are pores in the leaf epidermis that form between pairs of guard cells. They allow $CO_2$ uptake for photosynthetic carbon assimilation at the expense of water loss via transpiration. As such, they provide the major route for gaseous exchange between the interior of the leaf and the atmosphere and can limit photosynthetic rates by 50% or more when demand exceeds water supply. Stomata exert a major control on the water and carbon cycles of the world, and their activity in crops has been a key factor in global atmospheric modelling and weather prediction for over a quarter of a century. Stomatal aperture is controlled by guard cell turgidity which responds to changes in atmospheric $CO_2$ concentration, light, atmospheric relative humidity, and abscisic acid (5-8), thereby regulating plant water use. Efforts to improve plant water use efficiency have focused on reducing stomatal density, despite its implicit penalty in carbon assimilation (3, 4). Approaches that circumvent the carbon:water trade-off pose greater challenges but also much promise. In particular, accelerating the kinetics of stomatal opening and closing could be used to promote carbon assimilation under high light intensities, while maintaining plant water status when carbon demand is low (3, 4).

There therefore exists a need to reduce transpiration rates from the stomata without affecting photosynthesis, particularly in crops with slow stomatal kinetics. This will ultimately lead to an increase in growth and/or yield in these crops. The present invention addresses this need.

SUMMARY OF THE INVENTION

Stomata serve dual and often conflicting roles, facilitating $CO_2$ influx into the plant leaf for photosynthesis and restricting water efflux via transpiration. Thus, strategies for reducing transpiration without a cost for photosynthesis must circumvent this inherent coupling of $CO_2$ and water vapour diffusion. In one example, we have expressed a synthetic, light-gated potassium channel, specifically a $K^+$ channel, BLINK1, in guard cells surrounding stomatal pores to enhance the solute fluxes that drive stomatal aperture. BLINK1 introduced a $K^+$ conductance and accelerated both stomatal opening in the light and closing following irradiation. Thus, we demonstrate the potential of enhancing stomatal kinetics to improve water use efficiency without penalty in carbon fixation.

Accordingly, in one aspect of the invention there is provided a method of increasing at least one of growth, yield, drought tolerance, water use efficiency and/or carbon assimilation in a plant, the method comprising expressing a light-gated potassium channel in cells of the stomatal complex.

In a preferred embodiment, the method increases both water use efficiency and carbon assimilation.

In one embodiment, the method comprises expressing a blue-light gated potassium channel.

In a preferred embodiment, the method comprises introducing and expressing in a plant a nucleic acid construct comprising a nucleic acid sequence encoding a light-gated potassium channel, preferably a blue-light gated potassium channel operably linked to a regulatory sequence. More preferably, the nucleic acid sequence encodes a blue-light gated potassium channel (BLINK1) as defined in SEQ ID NO: 3 or a functional variant or fragment thereof. In a further preferred embodiment, the nucleic acid sequence encoding a blue-light induced potassium channel comprises a sequence as defined in SEQ ID NO: 4 or a functional variant or fragment thereof.

In one embodiment, the regulatory sequence is a stomatal complex promoter or a constitutive promoter. In a preferred embodiment, the stomatal complex promoter is a guard-cell specific promoter.

In another aspect of the invention, there is provided a nucleic acid construct comprising a nucleic acid sequence encoding a light-gated potassium channel operably linked to a regulatory sequence, wherein the regulatory sequence is a stomatal complex promoter.

In one embodiment, the potassium channel is a blue-light gated potassium channel or a red-light gated potassium channel, more preferably a blue-light gated potassium channel.

In one embodiment, the nucleic acid sequence encodes a blue-light gated potassium channel comprising a potassium channel as defined in SEQ ID NO: 1 or a functional variant or fragment thereof. More preferably, the nucleic acid sequence encoding the potassium channel comprises a sequence as defined in SEQ ID NO: 2 or a functional variant or fragment thereof.

In a preferred embodiment, the nucleic acid sequence encodes a blue-light gated potassium channel (BLINK1) as defined in SEQ ID NO: 3 or a functional variant or fragment thereof. More preferably, the nucleic acid sequence encoding a blue-light induced potassium channel comprises a sequence as defined in SEQ ID NO: 4 or a functional variant or fragment thereof.

In a preferred embodiment, the stomatal complex promoter is a guard cell-specific promoter. More preferably, the guard-cell specific promoter is selected from Myb60, GC1 and SNAC1.

In another aspect of the invention, there is provided a vector comprising the nucleic acid construct described above. In a further aspect there is provided a host cell comprising the nucleic acid construct or the vector described above.

In another aspect of the invention there is provided a transgenic plant expressing the nucleic acid construct or the vector described above.

In another aspect of the invention, there is provided a method of producing a transgenic plant as described above, the method comprising:
 a. selecting a part of the plant;
 b. transfecting at least one cell of the part of the plant of part (a) with the nucleic acid construct or the vector described above; and c. regenerating at least one plant derived from the transfected cell or cells.

In a final aspect of the invention, there is provided a plant obtained or obtainable by the method described above.

In one embodiment the plant is a monocot or dicot.

DESCRIPTION OF THE FIGURES

The invention is further described in the following non-limiting figures:

FIG. 4 shows gas exchange characteristics of BLINK1 transgenic and wild type plants adapted to either darkness or red light.

FIG. 5 shows growth characteristics of BLINK1-transgenic, wild type and p1p2 plants grown under two continuous light regimes; and under fluctuating light and two water regimes.

DETAILED DESCRIPTION OF THE INVENTION

Figure 1:
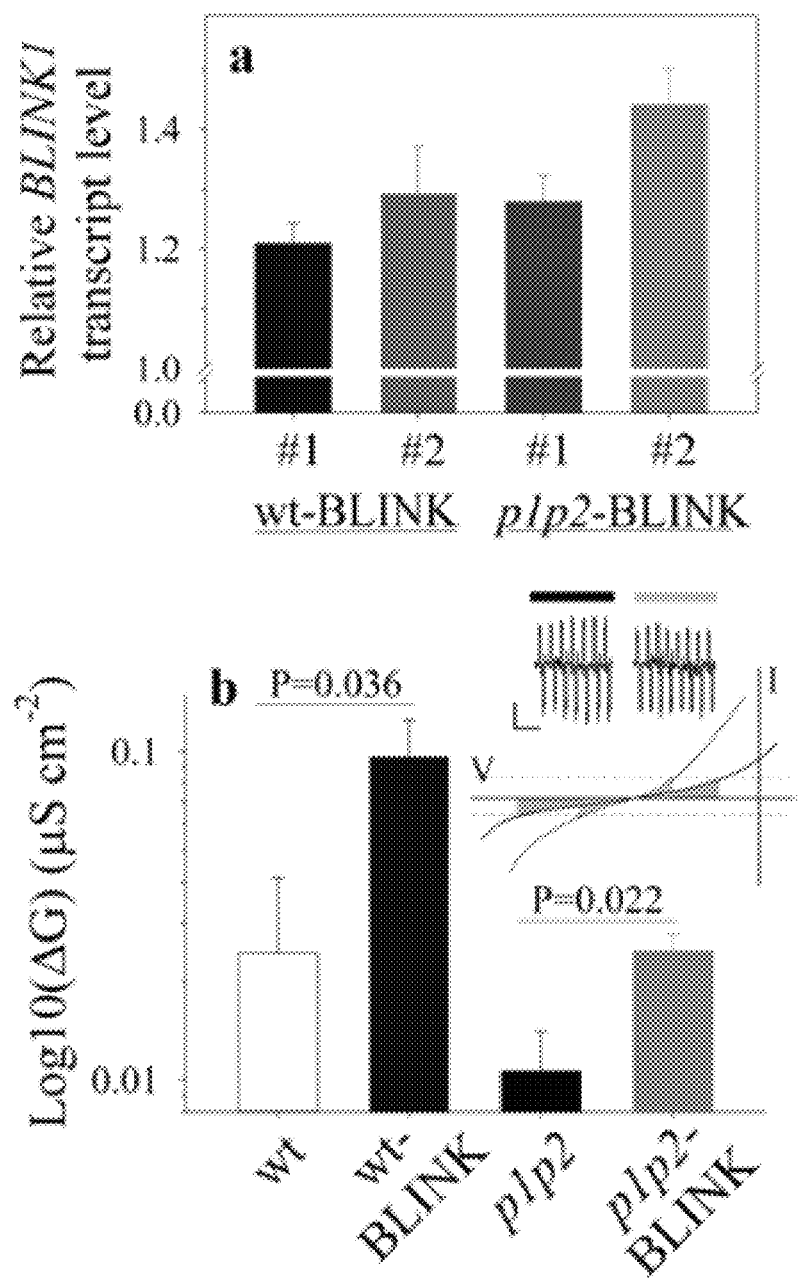
FIG. 1 shows that BLINK1 expression in planta facilitates K+ fluxes across the guard cell plasma membrane. (a) qRT-PCR analysis of relative BLINK1 transcript levels normalised to reference gene ISU(29) (n=4). (b) Change in membrane conductance ±BL as means±SE (n=4). Significance determined by student's t-test: wt/wt-BLINK, p=0.036; p1p2/p1p2-BLINK, P=0.022. Inset (above): Voltage deflections on current clamp with ±100 pA in 0.5-s steps. Scale bar: 10 mV, vertical, 5 s, horizontal. Inset (below): Schematic to show the consequence for fixed-amplitude current steps on membrane voltage before (black) and during (blue) BL to introduce an increase in conductance. Grey and blue shading indicates the range of voltage deflections. Dotted lines indicate current clamp amplitude.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The practice of the present invention will employ, unless otherwise indicated, conventional techniques of plant biology, microbiology, tissue culture, molecular biology, chemistry, biochemistry and recombinant DNA technology, bioinformatics which are within the skill of the art. Such techniques are explained fully in the literature.

As used herein, the words "nucleic acid", "nucleic acid sequence", "nucleotide", "nucleic acid molecule" or "polynucleotide" are intended to include DNA molecules (e.g., cDNA or genomic DNA), RNA molecules (e.g., mRNA), natural occurring, mutated, synthetic DNA or RNA molecules, and analogs of the DNA or RNA generated using nucleotide analogs. It can be single-stranded or double-stranded. Such nucleic acids or polynucleotides include, but are not limited to, coding sequences of structural genes, anti-sense sequences, and non-coding regulatory sequences that do not encode mRNAs or protein products. These terms also encompass a gene. The term "gene" or "gene sequence" is used broadly to refer to a DNA nucleic acid associated with a biological function. Thus, genes may include introns and exons as in the genomic sequence, or may comprise only a coding sequence as in cDNAs, and/or may include cDNAs in combination with regulatory sequences.

The terms "polypeptide" and "protein" are used interchangeably herein and refer to amino acids in a polymeric form of any length, linked together by peptide bonds.

The aspects of the invention involve recombination DNA technology and exclude embodiments that are solely based on generating plants by traditional breeding methods.

For the purposes of the invention, a "genetically altered plant" or "mutant plant" is a plant that has been genetically altered compared to the naturally occurring wild type (WT) plant. In one embodiment, the genetically altered plant is a transgenic plant. For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or (b) genetic control sequence(s) which is operably linked with the nucleic acid sequence according to the invention, for example a promoter, or (c) a) and b) are not located in their natural genetic environment or have been modified by recombinant methods, it being possible for the modification to take the form of, for example, a substitution, addition, deletion, inversion or insertion of one or more nucleotide residues.

The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815 both incorporated by reference.

In one aspect of the invention there is provided a method of increasing at least one of growth, yield, drought tolerance, water use efficiency (WUE) and/or carbon assimilation in a plant, the method comprising expressing a light-gated potassium channel in cells of the stomatal complex. In a preferred embodiment, there is provided a method of increasing growth and/or yield and/or water use efficiency and carbon assimilation. In other words, the method increases both water use efficiency and carbon assimilation.

The term "yield" in general means a measurable produce of economic value, typically related to a specified crop, to an area, and to a period of time. Individual plant parts directly contribute to yield based on their number, size and/or weight. The actual yield is the yield per square meter for a crop per year, which is determined by dividing total production per year (includes both harvested and appraised production) by planted square metres.

The term "increased yield" as defined herein can be taken to comprise any or at least one of the following and can be measured by assessing one or more of (a) increased biomass (weight) of one or more parts of a plant, aboveground (harvestable parts), or increased root biomass, increased root volume, increased root length, increased root diameter or increased root length or increased biomass of any other harvestable part. Increased biomass may be expressed as g/plant or kg/hectare, (b) increased seed yield per plant, which may comprise one or more of an increase in seed biomass (weight) per plant or on an individual basis, (c) increased seed filling rate, (d) increased number of filled seeds, (e) increased harvest index, which may be expressed as a ratio of the yield of harvestable parts such as seeds over the total biomass, (f) increased viability/germination efficiency, (g) increased number or size or weight of seeds or pods or beans or grain (h) increased seed volume (which may be a result of a change in the composition (i.e. lipid (also referred to herein as oil)), protein, and carbohydrate total content and composition, (i) increased (individual or average) seed area, (j) increased (individual or average) seed length, (k) increased (individual or average) seed perimeter, (l) increased growth or increased branching, for example inflorescences on more branches, (m) increased fresh weight or grain fill (n) increased ear weight (o) increased thousand kernel weight (TKW), which may be taken from the number of filled seeds counted and their total weight and may be as a result of an increase in seed size and/or seed weight (p) decreased number of barren tillers per plant and (q) sturdier or stronger culms or stems. All parameters are relative to a wild-type or control plant. The terms "seed" and "grain" as used herein can be used interchangeably. The terms "increase", "improve" or "enhance" as used herein are also interchangeable.

In one embodiment, an increase in yield comprises at least an increase in biomass, and in one embodiment, said increase in biomass is at least one-fold, two-fold, three-fold or four-fold or more compared to a wild-type or control plant. In one embodiment, the method increases biomass by at least two-fold compared to a wild-type or control plant.

In one embodiment, the method increases at least protein and/or starch composition in the plant.

By "water use efficiency" or "WUE" is meant the ratio of water used in plant metabolism to water lost through transpiration. In one example, WUE may be measured by measuring the amount of carbon fixed per water transpired. Alternatively, WUE may be measured by measuring the biomass per water transpired over a growing period or the amount of water fed to a plant. Other methods for measuring WUE would be well known to the skilled person.

By "carbon assimilation" or carbon fixation (such terms may be used interchangeably) is meant the conversion of inorganic carbon to organic compound, for example, through photosynthesis. In one example, carbon assimilation may be measured by measuring total biomass over time.

An "increase" as used herein, may refer to an increase of at least 1%, 2%, 3%, 4%, 5%, 6%, 7%, 8%, 9%, 10%, 20%, 30%, 40%, 50%, 60%, 70%, 80%, 90 or 95% or more compared to a control plant.

In some plants, stomatal opening (and closing) is controlled solely by guard cells. In other plants, such as maize and other grasses, stomatal opening (and closing) is controlled by a complex of pore-forming guard cells and adjacent subsidiary cells.

Accordingly, in one embodiment, the "cells of the stomatal complex" refers only to the guard cells. In other embodiments, the "cells of the stomatal complex" refer to the guard cells and adjacent subsidiary cells. In this embodiment, the light-gated potassium channel may be expressed in the guard cells and/or the subsidiary cells.

Preferably expression of a light-gated potassium channel in the stomatal complex affects stomatal opening, and more preferably increases the rate of stomatal opening and/or closing compared to a wild-type or control plant. In a particularly preferred embodiment, the light-gated potassium channel is a non-native or natural light-gated potassium channel. That is, the potassium channel is not an endogenous light-gated potassium channel—the channel is "exogenous" to an individual plant, which is introduced into the plant by any means other than by a sexual cross. As such, the method comprises the expression of a non-native channel. Examples of means by which this can be accomplished are described below. However, in another preferred embodiment, the potassium channel is a native channel.

The closing and opening of stomata is regulated by various parameters, which include endogenous light-activated signalling pathways. One such pathway acts through the photoreceptor proteins, phototropins. Phototropins are activated in response to blue light and lead, through a multi-component signalling cascade, to the opening of stomata.

Accordingly, by "light-gated potassium channel" is meant a transmembrane protein (i.e. the potassium channel) coupled with a photoswitch or photosensory molecule. Binding of photons to the photosensory molecule alters the confirmation of the channel, either to an open or closed state which in turn alters the conductance of the channel. Accordingly, in one embodiment, the light-gated potassium channel comprises a transmembrane potassium channel and a photosensory molecule. In one embodiment, binding of light to the channel causes the channel to open. In an alternative embodiment, binding of light to the channel causes the channel to close. Preferably, the channel is reversible. That is, in the presence/absence of light the channel can move from an open or closed position or vice versa. In a further embodiment, the photosensory molecule alters the confirmation of the transmembrane channel in response to a wavelength of light ranging from 280-800 nm or more preferably in response to a wavelength of light in the visible spectrum. The selectivity of the channel for a particular light is determined by the choice of photosensory molecule. However, in one preferred embodiment, the photosensory molecule alters the confirmation of the transmembrane channel in response to blue light.

Thus, in one embodiment the channel is a blue-light gated channel. Blue light may be defined as light between 390-495 nm. In one embodiment, the channel may open in response to blue light. In an alternative embodiment, the channel may close in response to blue light. In this example, a blue light-activated channel has the advantage that the channel will be activated at the same time as phototropins thereby leading to augmented stomatal opening.

In an alternative embodiment, the channel is a red-light gated channel. Red light may be defined as light between 600 to 750 nm. In one embodiment, the channel may open in response to red light. In an alternative embodiment, the channel may close in response to red light.

In one embodiment, the photosensory molecule comprises a phototropin, more preferably a phototropin fragment. In one embodiment, the phototropin fragment is a LOV2 domain.

In one embodiment, the LOV2 domain comprises or consists of the following sequence or a functional variant or fragment thereof:

```
                                        (SEQ ID NO: 14)
LATTLERIEKNFVITDPRLPDNPIIFASDS

FLQLTEYSREEILGRNCRFLQGPETDRATV

RKIRDAIDNQTEVTVQLINYTKSGKKFWNL

FHLQPMRDQKGDVQYFIGVQLDGTEHVRDA

AEREGVMLIKKTAE
```

In a further preferred embodiment, the photosensory molecule comprises at least one Jalpha helix domain. Preferably, the Jalpha helix domain comprises or consists of the following sequence or a functional variant or fragment thereof:

```
                                        (SEQ ID NO: 15)
AAEREGVMLIKKTAE
```

In an alternative embodiment, the photosensory molecule is selected from one of the following: a UV responsive protein (such as UVR8), a cryptochrome (such as CRY1 or CRY2), a phytochrome, a phototropin, a Zeitlupe (ZTL) family protein, a neochrome, an aureochrome, a BLUF-domain containing protein, a LOV-domain containing protein or a functionally active fragment thereof (that is, the fragment can respond to light and cause the opening and/or closing of a transmembrane potassium channel that is coupled to the photosensory molecule). In one embodiment, the fragment is under 20 kDa.

In one embodiment, the potassium channel itself is a native or non-native channel. That is the potassium channel may be the endogenous potassium channel that is coupled to a photosensory molecule, such as those described above. For example, where the plant is *Arabidopsis*, the potassium channel may be a KAT1 (NC_003076.8) or KAT2 (NC_003075.7) channel. In another example, where the plant is maize, the potassium channel may be a KZM2 (AY919830.1) or KZM3 (NM_001111691.1) channel. In another example, the native potassium channel is GORK. In one embodiment, the amino acid sequence of GORK is defined in SEQ ID NO: 10 and the nucleotide sequence defined in SEQ ID NO: 11. Also covered are functional variants and fragments thereof. Other endogenous potassium channels would be well known to the skilled person.

In an alternative embodiment, the potassium channel may be an exogenous channel. In one example, the channel may be a viral potassium channel, for example, Kcv. In one embodiment, the amino acid sequence of Kcv is defined in SEQ ID NO: 1 and the nucleotide sequence of Kcv is defined in SEQ ID NO: 2. Also covered are functional variants and fragments of these sequences, as defined below.

In one particularly preferred embodiment, the potassium channel is a blue-light gated potassium channel. In one example, the blue-light gated potassium channel is the BLINK1 channel or a variant thereof described below and in Cosentino et al., 2015, which is incorporated herein by reference. The BLINK1 channel is a fusion of the plant LOV2-Japha photosensory molecule to the small viral potassium channel, Kcv. The amino acid sequence of BLINK1 is defined in SEQ ID NO: 3 and the nucleotide sequence of BLINK1 is defined in SEQ ID NO: 4. BLINK1 acts as both a potassium efflux and influx channel, depending on the potassium concentration across the membrane, and is activated in response to blue-light leading to channel opening.

In one embodiment, a variant of BLINK1 comprises an amino acid sequence as defined in SEQ ID NO: 8 and a nucleic acid sequence as defined in SEQ ID NO: 9 or variants thereof. In this example, the BLINK1 variant is inhibited rather than activated by light.

In a further embodiment, a variant of BLINK1 comprises one or more amino acid substitutions, deletions or additions compared to the sequence presented in SEQ ID NO: 3. Preferably, the one or more amino acid substitutions, deletions or additions increases or decreases photoseneistivity. Preferably, the variant comprises one or more substitutions. Even more preferably, the variant comprises a 1427V substitution, and decreases LOV2 photosensitivity. In an alternative example, the variant comprises a V416I substitution and increases LOV2 photosensitivity.

As discussed above, in one embodiment, the method comprises expressing an exogenous light-gated potassium channel. In one example this may be achieved by introducing and expressing in the plant a nucleic acid construct comprising a nucleic acid sequence that encodes a light-gated potassium channel that is operably linked to a regulatory sequence. Examples of suitable light-gated and in particular blue-light gated potassium channels are described above.

In one embodiment, the method comprises introducing and expressing in the plant a nucleic acid construct comprising a nucleic acid sequence that encodes a light-gated potassium channel that is operably linked to a regulatory sequence, wherein the nucleic acid sequence encodes a blue-light gated potassium channel. In one embodiment, the potassium channel is defined in SEQ ID NO: 1, more preferably a blue-light gated potassium channel as defined in SEQ ID NO: 3 or a functional variant or fragment thereof.

In a more preferred embodiment, the nucleic acid construct comprises a nucleic acid sequence as defined in SEQ ID NO: 4 or a functional variant or fragment thereof.

The term "variant" or "functional variant" as used throughout with reference to any of the sequences described herein refers to a variant gene sequence or part of the gene sequence (such as a fragment) which retains the biological function of the full non-variant sequence. A functional variant also comprises a variant of the gene of interest, which has sequence alterations that do not affect function, for example in non-conserved residues. Also encompassed is a variant that is substantially identical, i.e. has only some sequence variations, for example in non-conserved residues, compared to the wild type sequences as shown herein and is biologically active. Alterations in a nucleic acid sequence that results in the production of a different amino acid at a given site that does not affect the functional properties of the encoded polypeptide are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

As used in any aspect of the invention described throughout a "variant" or a "functional variant" has at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to the non-variant nucleic acid or amino acid sequence.

The term "operably linked" as used throughout refers to a functional linkage between the promoter sequence and the gene or nucleotide sequence of interest, such that the promoter sequence is able to initiate transcription of the gene or nucleotide sequence of interest.

In a preferred embodiment of the invention, the regulatory sequence may be a promoter. According to all aspects of the invention, including the method above and including the plants, methods and uses as described below, the term "regulatory sequence" is used interchangeably herein with "promoter" and all terms are to be taken in a broad context to refer to regulatory nucleic acid sequences capable of effecting expression of the sequences to which they are ligated. The term "regulatory sequence" also encompasses a synthetic fusion molecule or derivative that confers, activates or enhances expression of a nucleic acid molecule in a cell, tissue or organ.

The term "promoter" typically refers to a nucleic acid control sequence located upstream from the transcriptional start of a gene and which is involved in the binding of RNA polymerase and other proteins, thereby directing transcription of an operably linked nucleic acid. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences.

More preferably the promoter may be a constitutive promoter. In an alternative embodiment, the promoter may be a tissue-specific promoter, preferably a stomatal complex-specific promoter (as defined above) and more preferably a guard-cell promoter.

A "constitutive promoter" refers to a promoter that leads to increased or overexpression of the target gene. Examples of strong promoters include, but are not limited to, CaMV-35S, CaMV-35Somega, ubiquitin, such as UB10 and actin.

In one example, a guard cell specific promoter may be selected from Myb60, GC1, and the SNAC1 promoter. In one embodiment, where the plant is a *Brassica* the promoter may be GC1 or Myb60. In another embodiment, where the plant is barley the promoter may be SNAC1 or GC1.pass In another embodiment, GC1 comprises a sequence as defined in SEQ ID NO: 7 or a functional variant, fragment or homolog or orthologue thereof.

In another embodiment, the promoter may be an epidermal promoter, which allows the light-gated potassium channel to be expressed in the subsidiary cells of the stomatal complex. Examples of epidermal promoters include CER6, ATML1, TaGstA1 and the maize CST1promoter. In one embodiment, where the plant is a *Brassica* the epidermal promoter may be CER6 or ATML1. In another embodiment, where the plant is barley, the epidermal promoter is TaGstA1 or the maize CST1promoter. In one example, the CER6 promoter sequence comprises or consists of the nucleic acid sequence defined in SEQ ID NO: 12 or a functional variant or fragment thereof. In another example, the TaGstA1 promoter sequence comprises or consists of the nucleic acid sequence defined in SEQ ID NO: 13 or a functional variant or fragment thereof Suitable homologs or orthologs can be identified by sequence comparisons and identification of conserved domains. The function of the homolog or ortholog can be identified as described herein and a skilled person would thus be able to confirm the function when expressed in a plant.

For the identification of functionally equivalent promoters, the promoter strength and/or expression pattern of a candidate promoter may be analysed for example by operably linking the promoter to a reporter gene and assaying the expression level and pattern of the reporter gene in various tissues of the plant. Suitable well-known reporter genes are known to the skilled person and include for example beta-glucuronidase or beta-galactosidase.

In a preferred embodiment of the methods described herein the organism is grown or cultured in fluctuating or continuous light conditions. In other words, the organism may be cultured in normal day and/or night conditions (i.e. this may mean that the plant is exposed to a suitable day/night cycle) or exposed to a fluctuating or continuous light regime. If the plant is to be grown indoors with LED lighting, the length, duration and wavelength of light may be controlled.

In an alternative embodiment, genome editing techniques may be used to express a light-gated potassium channel in the cells of the stomatal complex. In one embodiment, CRISPR may be used to introduce one or more copies of an light-gated potassium channel as described above into the genome at an appropriate place, that is under the control of a suitable promoter, such as the promoters described in this application.

In another aspect of the invention, there is provided a method of increasing stomatal opening and/or closing and/or accelerating stomatal kinetics, the method comprising expressing a light-gated potassium channel in cells of the stomatal complex, as described above.

In another aspect of the invention there is provided a nucleic acid construct comprising a nucleic acid sequence encoding a light gated potassium channel as described above operably linked to a regulatory sequence, wherein the regulatory sequence is a stomatal complex promoter, as described above.

In another aspect of the invention, there is provided a vector or expression vector comprising the nucleic acid construct described herein.

In another aspect of the invention there is provided a host cell comprising the nucleic acid construct or the vector. Preferably the host cell is a plant cell.

In another aspect of the invention there is provided a transgenic plant where the transgenic plant expresses the nucleic acid construct or vector.

In one embodiment, the progeny plant is transiently transformed with the nucleic acid construct or vector. In another embodiment, the progeny plant is stably transformed with the nucleic acid construct described herein and comprises the exogenous polynucleotide encoding the light gated potassium channel which is heritably maintained in at least one cell of the organism. The method may include steps to verify that the construct is stably integrated. The method may also comprise the additional step of collecting seeds from the selected progeny plant.

In a further aspect of the invention there is provided a method of producing a transgenic plant as described herein, the method comprising at least the following steps:
a. selecting a part of the plant;
b. transfecting at least one cell of the part of the plant of part (a) with the nucleic acid construct or the vector; and
c. regenerating at least one plant derived from the transfected cell or cells.

Transformation or transfection methods for generating a transgenic plant of the invention are known in the art. Thus, according to the various aspects of the invention, a nucleic acid construct as defined herein is introduced into an organism and expressed as a transgene. The nucleic acid construct is introduced into said organism through a process called transformation. The term "transfection", "introduction" or "transformation" as referred to herein encompasses the transfer of an exogenous polynucleotide into a host cell, irrespective of the method used for transfer. Such terms can also be used interchangeably in the present context. Where the organism is a plant, tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

Transformation of plants is now a routine technique in many species. Advantageously, any of several transformation methods may be used to introduce the gene of interest into a suitable ancestor cell. The methods described for the transformation of an organism's cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts, electroporation of protoplasts, microinjection into plant material, DNA or RNA-coated particle bombardment, infection with (non-integrative) viruses and the like. Transgenic plants, including transgenic crop plants, are preferably produced via *Agrobacterium tumefaciens* mediated transformation.

To select transformed plants, the plant material obtained in the transformation is subjected to selective conditions so that transformed plants can be distinguished from untransformed plants. For example, the seeds obtained in the above-described manner can be planted and, after an initial growing period, subjected to a suitable selection by spraying. A further possibility is growing the seeds, if appropriate after sterilization, on agar plates using a suitable selection agent so that only the transformed seeds can grow into plants. Alternatively, the transformed plants are screened for the presence of a selectable marker or expression of a constitutively expressed reporter gene, as described above. Following DNA transfer and regeneration, putatively transformed plants may also be evaluated, for instance using Southern blot analysis, for the presence of the gene of interest, copy number and/or genomic organisation. Alternatively or additionally, expression levels of the newly introduced DNA may be monitored using Northern and/or Western blot analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

In a further aspect of the invention, there is provided a plant obtained or obtainable by the methods described herein.

In a final aspect of the invention, there is provided the use of the nucleic acid construct or vector as described herein to increase at least one of growth, yield, drought tolerance, WUE and carbon assimilation.

A plant according to all aspects of the invention described herein may be a monocot or a dicot plant. Preferably, the plant is a crop plant. By crop plant is meant any plant which is grown on a commercial scale for human or animal consumption or use. In a preferred embodiment, the plant is a cereal. In another embodiment the plant is *Arabidopsis*.

The plant according to the various aspects of the invention may be a moncot or a dicot plant. A dicot plant may be selected from the families including, but not limited to Asteraceae, Brassicaceae (eg *Brassica napus*), Chenopodiaceae, Cucurbitaceae, Leguminosae (Caesalpiniaceae, Aesalpiniaceae Mimosaceae, Papilionaceae or Fabaceae), Malvaceae, Rosaceae or Solanaceae. For example, the plant may be selected from lettuce, sunflower, *Arabidopsis*, broccoli, spinach, water melon, squash, cabbage, tomato, potato, yam, *capsicum*, tobacco, cotton, okra, apple, rose, strawberry, alfalfa, bean, soybean, field (fava) bean, pea, lentil, peanut, chickpea, apricots, pears, peach, grape vine or citrus species. In one embodiment, the plant is oilseed rape.

Also included are biofuel and bioenergy crops such as rape/canola, sugar cane, sweet sorghum, *Panicum virgatum* (switchgrass), linseed, lupin and willow, poplar, poplar hybrids, *Miscanthus* or gymnosperms, such as loblolly pine. Also included are crops for silage (maize), grazing or fodder (grasses, clover, sanfoin, alfalfa), fibres (e.g. cotton, flax), building materials (e.g. pine, oak), pulping (e.g. poplar), feeder stocks for the chemical industry (e.g. high erucic acid oil seed rape, linseed) and for amenity purposes (e.g. turf grasses for golf courses), ornamentals for public and private gardens (e.g. snapdragon, *petunia*, roses, geranium, *Nicotiana* sp.) and plants and cut flowers for the home (African violets, Begonias, chrysanthemums, geraniums, *Coleus* spider plants, Dracaena, rubber plant).

A monocot plant may, for example, be selected from the families Arecaceae, Amaryllidaceae or Poaceae. For example, the plant may be a cereal crop, such as wheat, rice, barley, maize, oat, sorghum, rye, millet, buckwheat, turf grass, Italian rye grass, sugarcane or *Festuca* species, or a crop such as onion, leek, yam or banana.

Preferably, the plant is a crop plant. By crop plant is meant any plant which is grown on a commercial scale for human or animal consumption or use. Preferred plants are maize, wheat, rice, oilseed rape, sorghum, soybean, potato, tomato, grape, barley, pea, bean, field bean, lettuce, cotton, sugar cane, sugar beet, broccoli or other vegetable brassicas or poplar.

The term "plant" as used herein encompasses whole plants, ancestors and progeny of the plants and plant parts, including seeds, fruit, shoots, stems, leaves, roots (including tubers), flowers, tissues and organs, wherein each of the aforementioned comprise the nucleic acid construct as described herein or carry the herein described mutations. The term "plant" also encompasses plant cells, suspension cultures, callus tissue, embryos, meristematic regions, gametophytes, sporophytes, pollen and microspores, again wherein each of the aforementioned comprises the nucleic acid construct or mutations as described herein.

The invention also extends to harvestable parts of a plant of the invention as described herein, but not limited to seeds, leaves, fruits, flowers, stems, roots, rhizomes, tubers and bulbs. The aspects of the invention also extend to products derived, preferably directly derived, from a harvestable part of such a plant, such as dry pellets or powders, oil, fat and fatty acids, starch or proteins. Another product that may be derived from the harvestable parts of the plant of the invention is biodiesel. The invention also relates to food products and food supplements comprising the plant of the invention or parts thereof. In one embodiment, the food products may be animal feed. In another aspect of the invention, there is provided a product derived from a plant as described herein or from a part thereof. In a most preferred embodiment, the plant part or harvestable part is a seed or the fruit. Therefore, in a further aspect of the invention, there is provided a seed or fruit produced from a genetically altered plant as described herein.

A control plant as used herein according to all of the aspects of the invention is a plant which has not been modified according to the methods of the invention. Accordingly, in one embodiment, the control plant does not express the nucleic acid construct as described above. In an alternative embodiment, the plant has not been genetically modified, as described above. In one embodiment, the control plant is a wild type plant. The control plant is typically of the same plant species, preferably having the same genetic background as the modified plant.

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

The foregoing application, and all documents and sequence accession numbers cited therein or during their prosecution ("appin cited documents") and all documents cited or referenced in the appin cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

The invention is now described in the following non-limiting examples.

Example 1

Here we have used the synthetic, Blue Light-INduced K+ channel 1 (BLINK1) as a tool for modulating guard cell K+ conductance and accelerating changes in stomatal aperture with light. We demonstrate that a strategy of enhancing stomatal kinetics is sufficient to promote photosynthetic carbon assimilation and water use efficiency (WUE). Thus, BLINK1, and related optogenetic tools offer ways to explore plant growth and its relationship to WUE without a cost in $CO_2$ availability for photosynthesis.

Opening and closing of stomata is driven by ion transport across the guard cell plasma membrane which, together with the metabolism of organic solutes, promotes water flux and changes in guard cell volume and turgor. Blue light (BL) triggers stomatal opening, among other responses, enhancing photosynthesis through the action of the phototropin receptor kinases phot1 and phot2 that lead to activation of guard-cell H+-ATPases, in turn promoting K+ uptake (5, 9, 10). We therefore explored whether stomatal opening could be augmented by tissue-specific expression of the optogenetic tool BLINK1.

Figure 6:
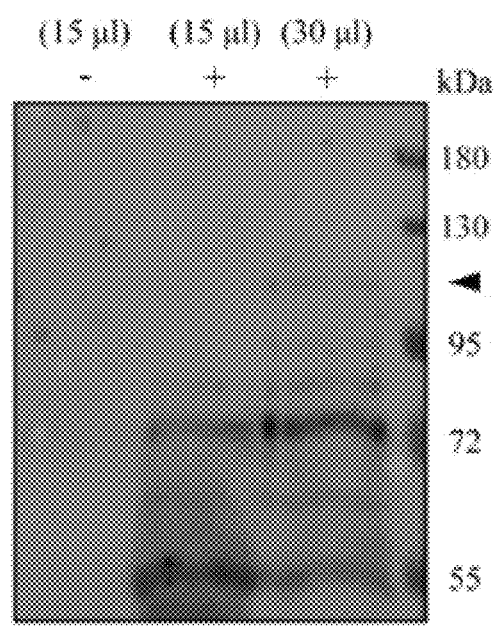
FIG. 6 shows functional tetramer formation of BLINK1 in planta. Immunoblot analysis of total protein extracts from *N. benthamiana* leaves BLINK1 (+) or not expressing BLINK1 (−). The protein extract volumes indicated were probed with anti-Kcv monoclonal antibody recognizing specifically the tetrameric form of the channel. Expected Mw of BLINK1 is 106.5 kDa. Lower Mw bands likely represent proteolytic cleavage products. Black arrow indicates the tetramer formation of BLINK1.

BLINK1 is a synthetic, blue light-gated K+ channel, constructed by fusing the LOV2-Jα photo-switch from *Avena sativa* phot1 to the small viral K+ channel Kcv; when expressed in human embryonic kidney cell cultures, it introduces a K+ conductance that is independent of voltage and activated by BL with half-maximal saturation near 40 µmol m-2 s-1 (11). To confirm that BLINK1 also functions in plants, initially we expressed BLINK1 transiently in tobacco and in *Arabidopsis* root epidermal cells (12). Immunoblots showed BLINK1 formed tetramers expected of the functional K+ channel (FIG. 6). On treatments with 100 µmol m-2 s-1 BL, membrane voltages of root epidermal cells bathed in 30 mM K+ showed mean displacements of 15 mV amplitude toward the predicted K+ equilibrium voltage, as expected on activating a K+ conductance (FIG. 5). From the voltage kinetics, we concluded that the conductance was fully activated within 2 min+BL and decayed over 8-10 min on transfer to dark.

To analyze BLINK1 function in guard cells, we used a strong guard cell-specific promoter (13) to express the synthetic channel in wild-type (wt) *Arabidopsis* (wt-BLINK) and, as a background control, in the phot1phot2 (p1p2) (14) double mutant (p1p2-BLINK). Transcript analysis showed that BLINK1 was expressed at comparable levels in two independent p1p2-BLINK and wt-BLINK transgenic lines (FIG. 1*b*). We measured the plasma membrane conductance using two-electrode recording methods (15) on intact guard cells of p1p2-BLINK and wt-BLINK transgenic lines, comparing conductances with each to the corresponding p1p2 and wt backgrounds. Close to the free-running voltage, the membrane conductance of *Arabidopsis* guard cells is normally small, making it difficult to resolve, by voltage clamp, the conductance changes that would suffice to enhance K+ flux and accelerate stomatal movements (Material & Methods). We therefore used a current clamp to drive 0.5-s steps of ±100 pA at intervals across the plasma membrane of dark-adapted guard cells isolated in epidermal peels. We monitored the resulting changes in voltage before, during, and after illuminating with 100 µmol m-2 s-1 BL (FIG. 1*b*, inset) and calculated the change in membrane conductance ±BL (ΔG) from Ohm's Law (FIG. 1*b*). Photo-activation of BLINK1 led to increased conductance in guard cells of p1p2-BLINK and of wt-BLINK plants compared to the p1p2 mutant and wt controls, respectively, with a 1.6-fold increase in ΔG of wt-BLINK plants (FIG. 1b). Thus, we concluded that BLINK1 introduces a BL-dependent K+ conductance in the plasma membrane of guard cells.

Figure 2:
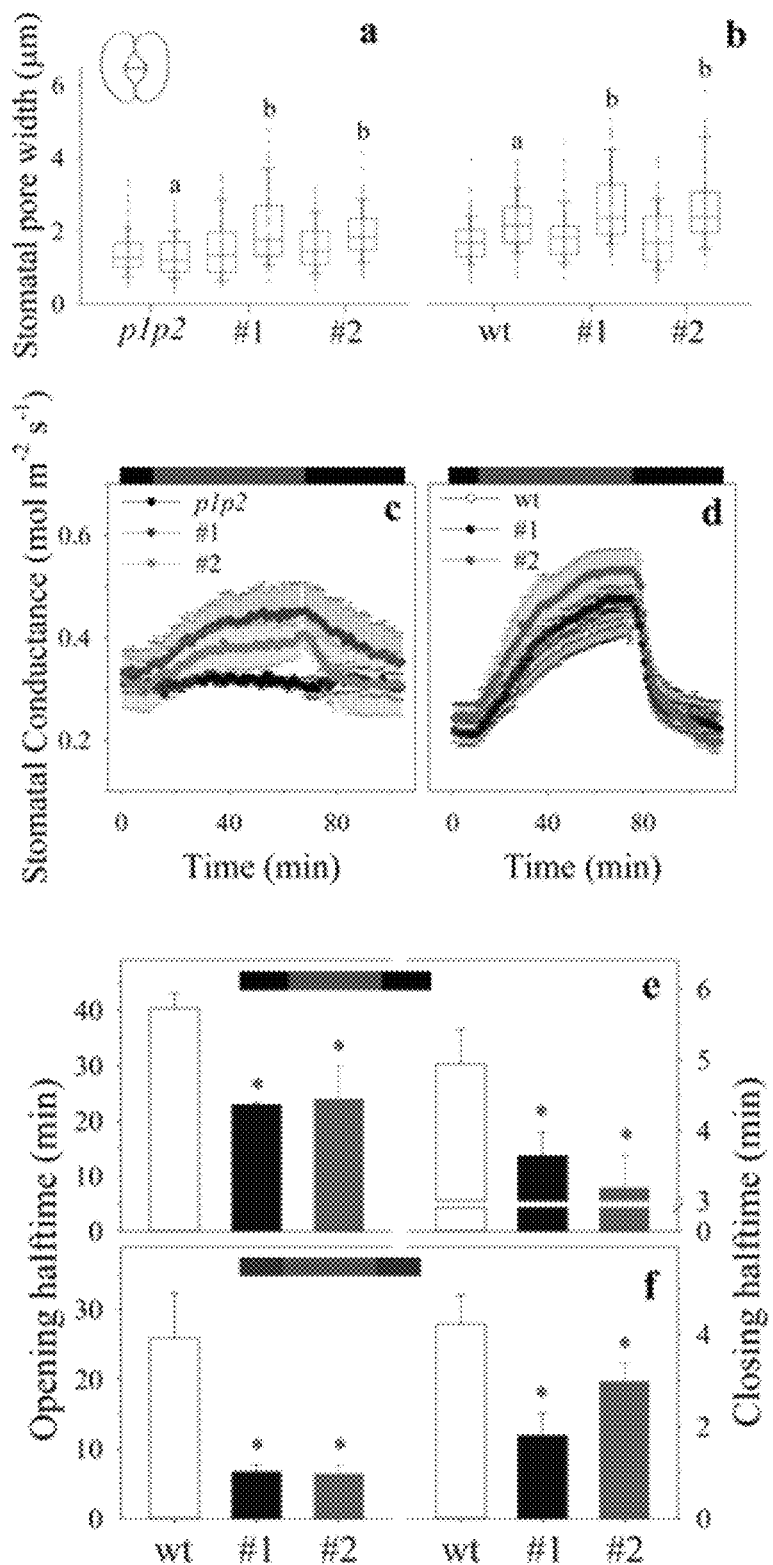
FIG. 2 shows BLINK1 photoactivation promotes stomatal opening and accelerates stomatal kinetics. (a,b) BLINK1 restoration of BL-induced stomatal opening in the p1p2 double mutant (a) and enhanced BL-induced stomatal opening in the wt background (b). Data are means±SE (n>100). Lettering indicates statistically significant differences from the wild-type and p1p2 backgrounds, as determined by Kruskal-Wallis ANOVA on Ranks (P<0.05). Inset: Schematic of stomatal pore width for measurement. (c,d) Stomatal conductances measured from p1p2 and p1p2-BLINK plants (c) and from wild-type and wt-BLINK plants (d) before, during and after 100 µmol m-2 s-1 BL treatments. (e,f) Halftimes for stomatal opening and closing of wt and wt-BLINK plants with steps from dark (e) and against a background of 100 µmol m-2 s-1 RL (f) were estimated by non-linear least-squares fitting of data following light transitions to a simple exponential function. Data are means±SE (n=5) from wt (white) and the two wt-BLINK lines (dark and light blue) in each case. Asterisks indicate statistically significant differences, as determined by student's t-test (P<0.05).

To examine whether BLINK1 photoactivation can alter stomatal opening, we recorded stomatal apertures in epidermal peels exposed to either red light (RL) or BL fluence rates of 100 µmol m-2 s-1 for 2 hours. BLINK1 restored BL-induced stomatal opening in the p1p2 double-mutant background (FIG. 2a) and enhanced the steady-state apertures of wt-BLINK plants on average by 17% compared to the wt background in BL (FIG. 2b). Similar apertures were observed for all plants under RL, indicating that the effects were BL-specific and demonstrating the potential for BLINK1 to augment stomatal opening in vivo. To assess stomatal kinetics with BLINK1, we used gas exchange and analysed the stomatal conductances of intact plants ±BL after dark and RL adaptation (FIG. 2c-f and FIG. 8). Compared to the wt, stomatal conductance was elevated in the p1p2 background in the dark, consistent with previous observations (16). Against this background, significant increases in stomatal conductance were recovered in each case in the p1p2-BLINK transgenics with 100 µmol m-2 s-1 BL, whereas p1p2 double-mutant plants were unresponsive to BL (FIG. 2c). BLINK1 expression in the wt background led to 22-29% enhancements in stomatal conductance in BL (FIG. 2d) despite a small reduction in stomatal size in one line. Mean stomatal opening and closing halftimes were accelerated by approximately 40% compared to the wt controls (FIG. 2e).

Figure 7:
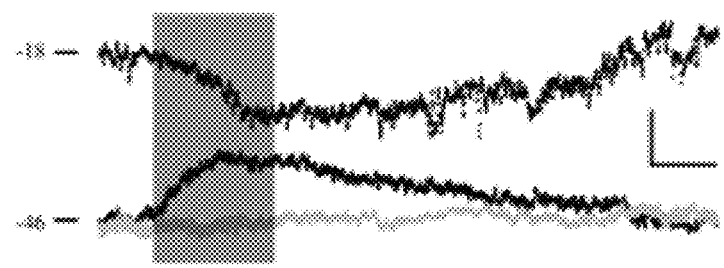
FIG. 7 shows BLINK1 photoactivation drives the membrane towards the K+ equilibrium voltage (EK). Representative recordings of membrane voltage in 5 mM Ca2+-MES, pH 6.1, with 30 mM KCl from wt (grey) and transiently BLINK1-transformed (black) *Arabidopsis* roots (12). Treatments with 100 µmol m-2 s-1 BL indicated by shading. Scale bar: 10 mV, vertical; 2 min, horizontal. Estimated EK, −30 mV. Mean halftimes and voltage displacements: 89±8 s (+BL); 351±24 s (−BL); 15±2 mV (n=10).
Figure 8:
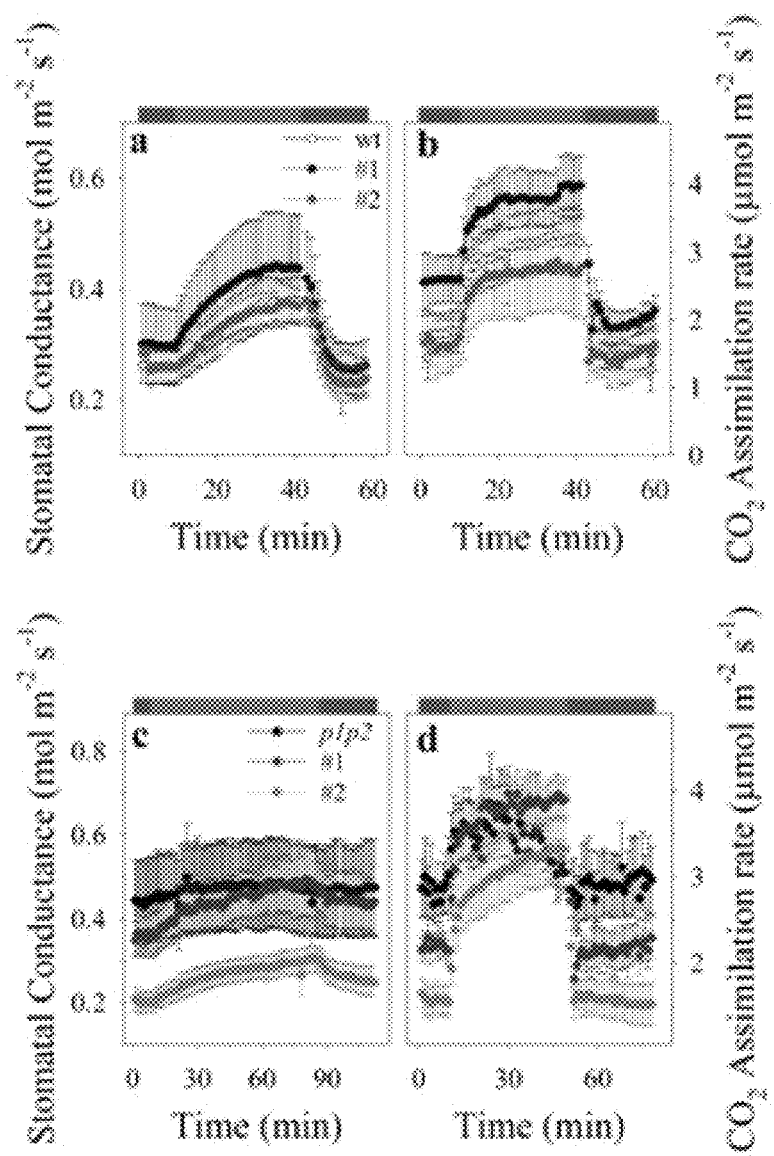
FIG. 8 shows BLINK1 photoactivation stimulates stomatal opening. Stomatal conductance (a, c) and CO2 assimilation rates (b, d) measured from RL-adapted wt, wt-BLINK, p1p2 and p1p2-BLINK plants on adding 100 µmol m-2 s-1 BL. Transitions from RL to RL+BL were carried out once stomatal conductances reached a steady state. Data are means±SE (n=5 for each line).

Pre-adapting plants to 200 µmol m-2 s-1 RL ensures a substantial background of photosynthetic energy input to reduce CO2 concentration within the leaf and reflects a more natural background for analyzing stomatal movements. As expected, no significant differences in steady-state transpiration, and hence in stomatal conductances, were observed between the wt-BLINK and wt plants; in this background, adding 100 µmol m-2 s-1 BL elevated stomatal conductance in all plants (FIG. 4). However, wt-BLINK plants showed accelerated changes in stomatal conductance, with 60-70% reductions in stomatal opening and closing halftimes compared to wt plants (FIG. 2f and FIG. 8). BLINK1 activity is independent of voltage and declined over 8-10 min (FIG. 1, FIG. 7 and (11)), so the accelerated kinetics for stomatal closing is consistent with BLINK1-promoted K+ efflux as well as influx subject to the electrochemical potential for K+ across the guard cell membrane.

Figure 9:
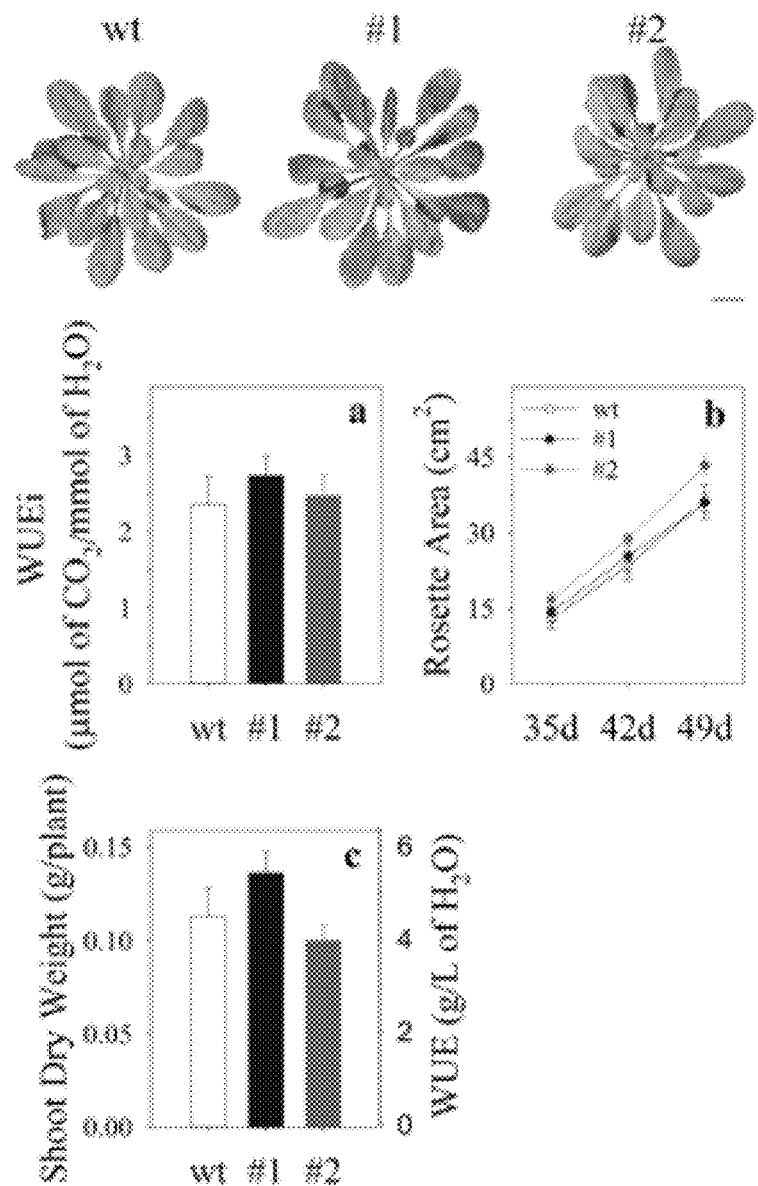
FIG. 9 shows BLINK1 has a marginal effect on carbon assimilation and WUE under diel cycles of continuous low light intensity. Wild type (white) and two wt-BLINK transgenic plants (dark and light blue bars and symbols) were grown under diel cycles of with steady illumination of 75 µmol m-2 s-1. Scale bar, 5 cm (above). (a) WUEi calculated from plants exposed to 75 µmol m-2 s-1 of homogeneous white light, at 390 ppm of CO2, 22° C. and 55% relative humidity. Data are means±SE (n=4 for each line). (b,c) Growth of plants followed for 49 days to measure rosette expansion (b) and accumulation of dry biomass and long term WUE (c). Data are means±SE (n=10 independent experiments).
Figure 10:
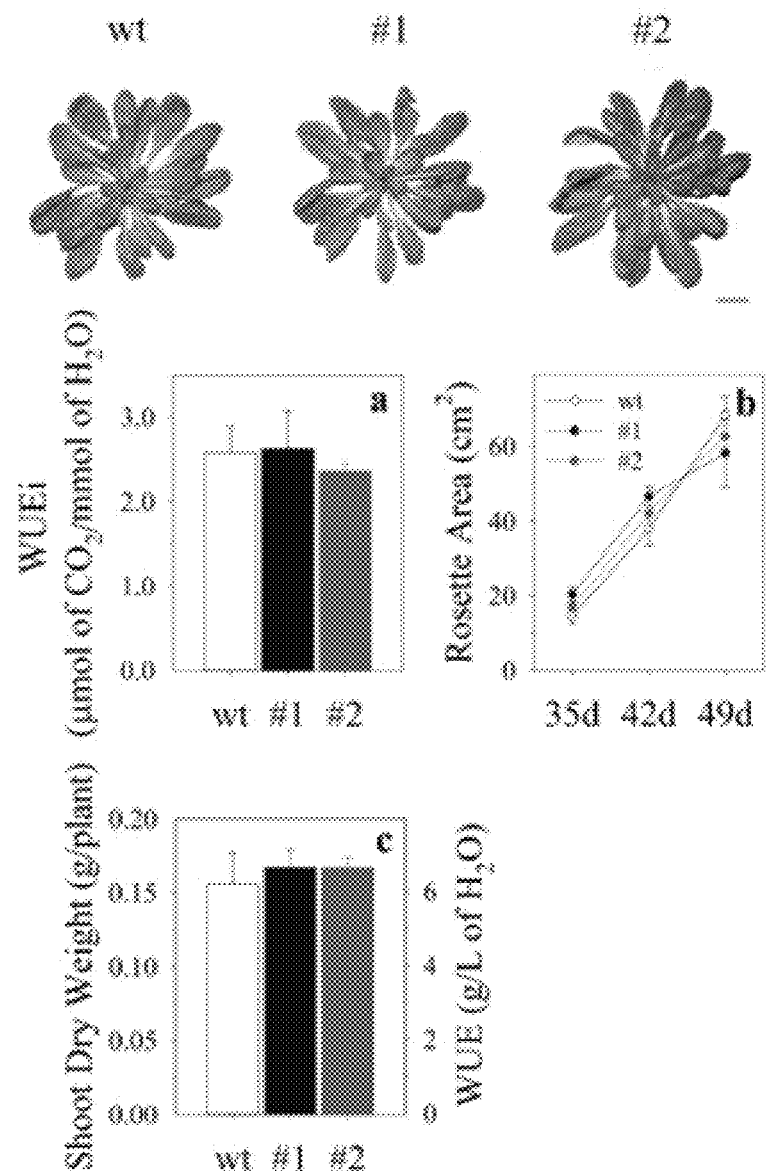
FIG. 10 shows BLINK1 has a marginal effect on carbon assimilation and WUE under diel cycles of continuous high light intensity. Wild type (white) and two wt-BLINK transgenic plants (dark and light blue bars and symbols) were grown under diel cycles of with steady illumination of 190 µmol m-2 s-1. Scale bar, 10 cm (above). (a) WUEi calculated from plants exposed to 190 µmol m-2 s-1 of homogeneous white light, at 390 ppm of CO2, 22° C. and 55% relative humidity. Data are means±SE (n=4 for each line). (b,c) Growth of plants followed for 49 days to measure rosette expansion (b) and accumulation of dry biomass and long term WUE (c). Data are means±SE (n=10 independent experiments).

One measure of plant productivity is water use efficiency, defined either as the amount of dry mass produced per unit water transpired (WUE) or as the ratio of the instantaneous rates of carbon assimilation over transpiration (WUEi). Both measures are affected by light through the combined influence on carbon demand and associated transpiration (17). We therefore examined the BLINK1 transgenic lines grown under diel cycles with daylight periods of constant white light, either at a low fluence rate (LWL) of 75 µmol m-2 s-1 or at a high fluence rate (HWL) of 190 µmol m-2 s-1. We calculated WUEi over these periods and determined WUE as the ratio of accumulated dry biomass to water used over the 49-day growth period. Under the LWL and HWL treatment, growth of wt-BLINK and p1p2-BLINK transgenic plants showed no significant differences in biomass accumulation, rosette area expansion, or water use when compared with that of the corresponding wt and p1p2 backgrounds (FIG. 9, FIG. 10 and FIG. 4).

Figure 3:
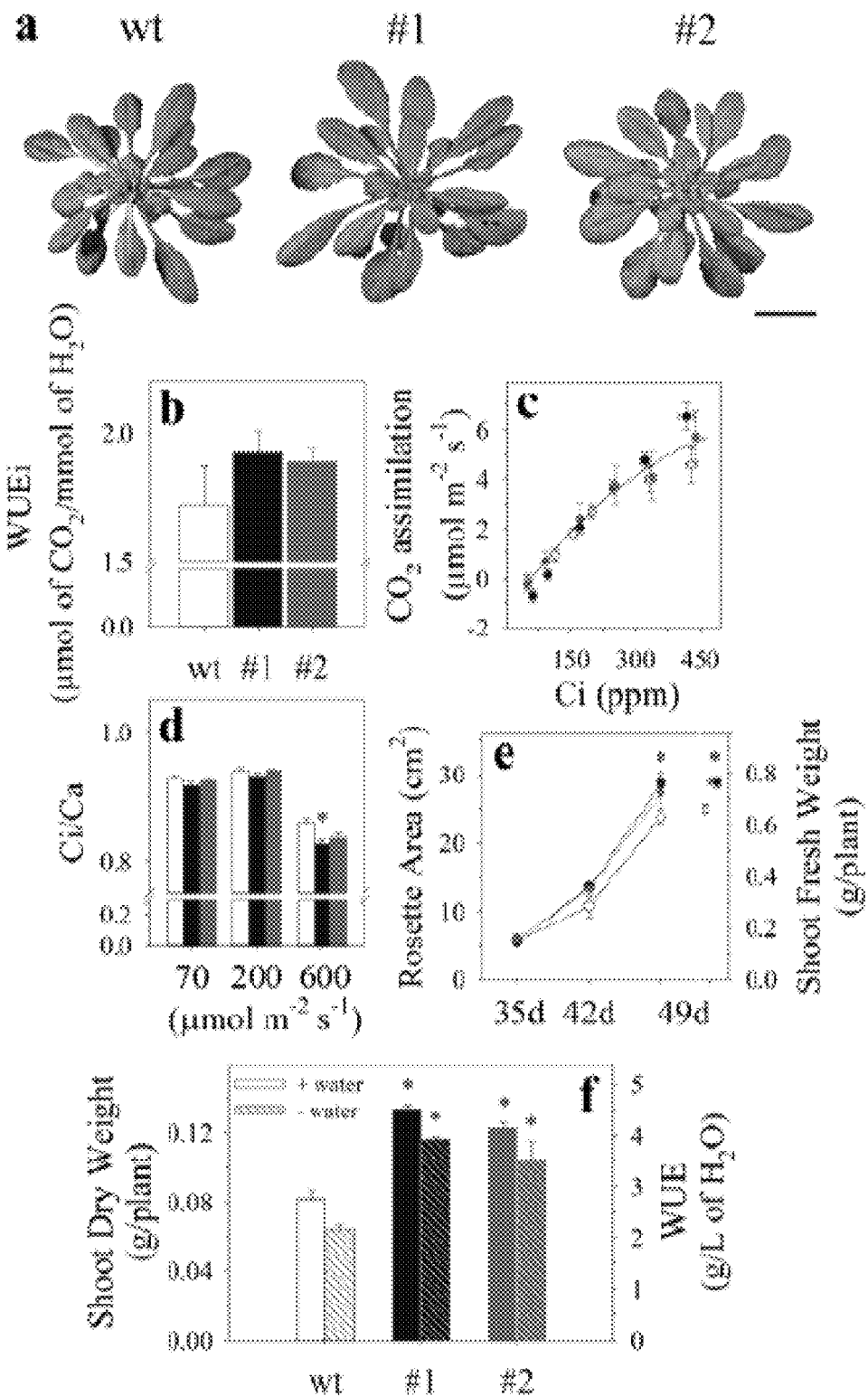
FIG. 3 shows BLINK1 expression enhances photosynthetic carbon assimilation and water use efficiency. Plants were grown under diel cycles with white light fluctuating at 1-h intervals between 10 to 150 µmol m-2 s-1, at 390 µL/L CO2, 22° C. and 55% relative humidity. Scale bar, 5 cm. (a) Representative wt (white) and two wt-BLINK plants (cross-referenced below in dark and light blue). (b) Instantaneous water use efficiency (WUEi), (c) relationship of CO2 assimilation to intracellular CO2 concentration (Ci) at saturating (1000 µmol m-2 s-1) white light and (d) Ci/Ca ratio at 70, 200 and 600 µmol m-2 s-1 of white light. Data are means±SE (n=4 for each line). (e,f) Long-term plant growth (e) measured as rosette area and WUE (f) determined for each experiment as dry biomass per liter of water applied. Data in (f) is for plants grown under water-replete (+water, open and solid bars) and water-deficient (−water, hatched bars) conditions. Data are means±SE (n=15 water-replete; n=6 water-deficit). Asterisks indicate statistically significant differences, determined by student's t-test (P<0.05).
Figure 11:
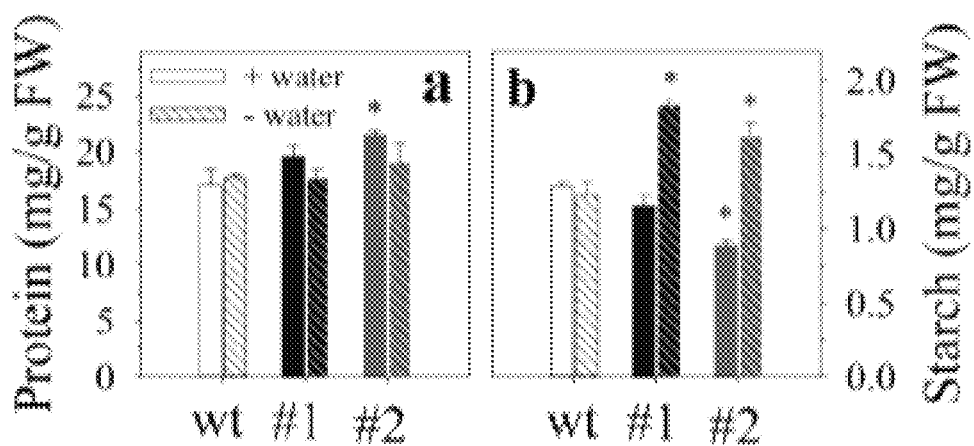
FIG. 11 shows BLINK1 induces starch accumulation under water limited conditions. Plants were grown under diel cycles with white light fluctuating at 1-h intervals between 10 to 150 µmol $m^{-2}$ $s^{-1}$, at 390 µL/L CO2, 22° C. and 55% relative humidity. Plants exposed to two water regimes, water-replete (+water; open and solid bars) and water-deficit (−water; hatched bars) with 10% soil moisture. a) Total protein amount and (b) total starch amount, quantified as mg per g of fresh shoot weight. Data are means±SE (n=4). Asterisks indicate statistically significant differences, determined by student's t-test (P<0.05).

In the natural environment light fluctuates, for example as clouds pass over. Photosynthesis generally tracks light energy input, but stomata are slower to respond. The slower stomatal kinetics limits gas exchange and can lead to suboptimal assimilation when fluence rate rises and to transpiration without corresponding assimilation when the fluence rate drops quickly (3, 17). Because BLINK1 accelerated stomatal movements (FIG. 2) we predicted that, when integrated over periods of fluctuating light, BLINK1 could benefit carbon assimilation and water use. We therefore examined the BLINK1 transgenic lines grown with daylight periods of fluctuating WL (FWL) to give a total photon flux over the daylight period intermediate to the two continuous light regimes. We stepped fluence rates ranging between 10 and 150 µmol m-2 s-1 at 60-min intervals, which is close to the time normally required for stomatal opening (FIG. 2) and therefore would maximize any advantages afforded by BLINK. No change was evident in WUEi (FIG. 3b). However, rosette area and fresh weight increased in wt-BLINK transgenic plants when compared to the wt control (FIG. 3b,e and FIG. 4) and we found a 2.2-fold increase in total dry biomass of plants grown under both water-replete and water-deficit conditions which, for similar rates of steady-state transpiration, translates to an equivalent and highly significant improvement in WUE in the wt-BLINK plants (FIG. 3f). We observed a modest increase in total protein content and decrease in starch in water-replete-grown plants, and a highly significant increase in total starch in water-deficit-grown plants (FIG. 11). The wt-BLINK plants showed significant decreases in fresh/dry weight ratios under both conditions (FIG. 5). Much of this biomass is likely therefore to be accounted for by changed in cell wall material. We confirmed that this increased biomass was not the consequence of alterations in photosynthesis per se (18): CO2 assimilation under saturating light (1000 µmol m-2 s-1) was unaffected in wt-BLINK plants across the physiological range of internal CO2 concentrations (FIG. 3c), and the Ci/Ca ratios determined at 70, 200 and 600 µmol m-2 s-1 of white light were similar to wt plants in each case (FIG. 3d). Thus, we conclude that guard-cell expression of BLINK1 and the accelerated stomatal kinetics afforded by the synthetic channel are responsible for enhancing carbon assimilation without a cost in water use.

Optogenetics has revolutionised the study of the mammalian nervous circuitry (11, 19). Because of the high output gain possible in regulating neuronal membrane voltage, the ion fluxes introduced by rhodopsin-based pumps and channels have proven sufficient to control rapid nervous signal transmission (20, 21). Introducing BLINK1 into guard cells now demonstrates the application potential for optogenetics to manipulate net ion flux in plant cells which, over periods of many minutes, can directly alter cell volume and osmotically-related physiology. As many plant 'movements', growth, and morphogenic phenomena rely on solute flux to drive turgor and cell expansion, optogenetics offers new strategies with which to study and control these processes. Our findings also have implications for strategies to improve crop WUE and enhance net photosynthetic carbon assimilation. Much research to date has focused on enhancing WUE by reducing stomatal densities, an approach that suppresses the overall conductance of the leaf but also reduces $CO_2$ availability for photosynthesis and can slow plant growth (3, 22-25). Manipulating the native populations of ion channels and pumps has been shown to affect stomatal conductance and photosynthesis, but generally at the expense of carbon assimilation or of WUE (15, 26-28). Indeed, a systems analysis of stomatal physiology shows that manipulating transporter populations alone is unlikely to improve stomatal performance and that alterations targeting the control of transport, including channel gating, are more likely to be effective (28). Our findings now demonstrate the efficacy of introducing new controls on guard cell membrane transport: incorporating BLINK1 adds a light-driven conductance that accelerates stomatal opening and closing to match the temporal demands for guard cell ion flux. Our findings highlight the gains that might be achieved by enhancing stomatal kinetics under changing light environments. Furthermore, we demonstrate that stomatal speed (3) can improve WUE without a cost in carbon assimilation. Enhancing guard cell ion flux with available light is an effective strategy to match stomatal movements with the often conflicting demands of safeguarding water use, at the same time gaining in photosynthetic assimilation during vegetative growth.

Material and Methods
Plant Material and Growth

Wild-type (wt) *Arabidopsis thaliana* L. Heynh. (gl-1, ecotype Columbia) and the double mutant phot1-5 phot2-1 (p1p2) were described previously (9). Plants were grown in short day conditions (8-h-light/16-h-dark cycle with, 22° C./18° C., and 60% and 70% relative humidity). Three daylight regimes were used for growth experiments, either with steady 75 or 190 µmol m-2 s-1 or with light stepped at 1-h intervals at light intensities ranging between 10 and 150 µmol m-2 s-1. For growth under water-deficit, after 21 d soil moisture was monitored daily with a Delta-T HH2-ML3 moisture sensor (Delta-T Devices, Cambridge UK) and maintained at 10% with water as required.

Stable Transformation

For stable transformations, the plasmid pEZR(K)-LN (30) was digested with SacI and BamHI. The primer pairs CTCACTATAGGGAGCTCACAAGGACACAAGGA-CATATG (SEQ ID NO: 16) and CATCCCAT-TAAGCCTGCTTTTTTGTACAAAC (SEQ ID NO: 17) were used to amplify the guard-cell promoter (pMYB60) (13, 31), and the primer pairs CAGGCTTAATGGGATGTA-CAGTCTCTGC (SEQ ID NO: 18) and CAGCGGCAGCAGCCGTCATAAAGTTAGAACGAT-GAAG (SEQ ID NO: 19) were used to amplify the BLINK1 coding sequence (11). The final pEZ pMYB60::BLINK1 construct was generated by Gibson Assembly. Transformation of *Arabidopsis thaliana* gl1 and phot1-5 phot2-1 (14) with *Agrobacterium* was performed as described previously (32). T3 lines with a single transgene locus were selected by segregation of the kanamycin resistance (33).

Transient Transformation of *Nicotiana benthamiana* and *Arabidopsis*

For transient expression of BLINK1 under the control of the CaMV 35S promoter in *N. benthamiana*, the entry clone was generated by PCR using specific primers containing attB3 5'-GGGGACAACTTTGTATAATAAAGTTGTCAA-CATGGGATGTACAGTCTCTGCAGAG-3' (SEQ ID NO: 20) and attB2 sites 5'-GGGGACCACTTTGTA-CAAGAAAGCTGGGTATCATAAAGTTAGAACGAT-GAAGAAC ACTG-3' (SEQ ID NO: 21). The gel purified PCR product was used together with the pDONR 221 P3-P2 vector to create the final DONR vector using BP-clonase II (Life technologies) according to the manufacturer's instructions. After verifying the product of the BP-reaction by sequencing, LR-clonase II (Life Technologies) was used together with the pFRET cg-2in1-cc vector (34) to generate the final destination vector pFRET cg-2in1-cc BLINK1/mCherry. Infiltration of *N. benthamiana* leaves was performed with transformed *Agrobacterium* as described previously (35). Transient transformation of *Arabidopsis* roots was performed as described previously (12).

Immunoblot Analysis

Total protein extracts were prepared from *N. benthamiana* leaf discs 3 days post infiltration. Plant tissue was ground with a pestle in SDS sample buffer (62.5 mM Tris-HCl, pH 6.8, 2% SDS, 10% glycerol, 5% 1 mM DTT, 0.004% bromophenol blue) and centrifuged at 10,000 g, at 4° C. for 5 min. Half of the supernatant was directly used for immunoblot analysis of the BLINK1 tetramer (unboiled sample). Protein samples were subjected to 7.5% SDS-PAGE detection for the BLINK1 tetramer. Proteins were transferred onto nitrocellulose membrane (BioRad) by electroblotting and detected with anti-Kcv antibody (36). Blots were developed with horseradish peroxidase (HRP)-linked secondary antibodies (Promega) and Pierce ECL Plus Western Blotting Substrate (Thermo Fisher Scientific).

Gas Exchange and Stomatal Aperture Analysis

Gas exchange measurements were carried out using the LI-COR 6400 XT Infrared Gas Analyzer (LICOR Biosciences) and whole-plant *Arabidopsis* chamber (LI-COR 6400-17) (37). Light was adjusted using an integrated RGB light source (LI-COR 6400-18). Stomatal conductance was calculated from transpiration rates at a temperature of 22° C. Measurements were carried out over the same period of the diurnal cycle and were normalised to rosette area calculated from images using ImageJ 1.43u (http://rsb.info.nih.gov/ij).

Apertures were recorded from stomata in epidermal peels continuously superfused with 5 mM $Ca^{2+}$-MES, pH 6.1, with 10 mM KCl (33, 37), in the dark and under RL and/or BL of 100 µmol m-2 s-1 for 2 h. Following measurements, the stomata were incubated for 5 min in buffer supplemented with 20 µM fluorescein diacetate to confirm viability. Only stomata with guard cells retaining a fluorescein signal under confocal fluorescence microscopy were included for analysis.

RNA extraction and real-time PCR

Total RNA was extracted from leaf tissue from 4-week old plants using Plant RNeasy Mini kit, and cDNA synthesis was carried out using Quanti-script (Qiagen) kit. Real-time PCR was carried out using Brilliant III Ultra-Fast SYBR QPCR kit (Applied Biosystems) with primer pairs ATG-GAACTGAGCATGTCCGA (SEQ ID NO: 22) and TTTTGTCCGGGTTTGCAACA (SEQ ID NO: 23) to amplify BLINK, and GCCATCGCTTCTTCATCTGTTGC (SEQ ID NO: 24) and GTGGGGAGAGAAA-GATGCTTTGCG (SEQ ID NO: 25) to amplify the reference ISU gene (29). For each transcript, amplification was assayed over a range of cycle numbers to select optimal conditions for visualization of the PCR product and quantification.

Guard Cell Electrophysiology

Voltages and current clamp data were recorded from *Arabidopsis* root epidermal cells and intact guard cells in epidermal peels using Henry's EP Software Suite (http://www.psrg.org.uk). Double-barrelled microelectrodes (tip resistances>100 MΩ) were filled with 200 mM K+-acetate (pH 7.5) as described previously (37-40) after equilibration against resin-bound BAPTA [for 1,2-bis(o-aminophenoxy)ethane-N,N,N9,N9-tetraacetic acid; Invitrogen] to prevent $Ca^{2+}$ loading of the cytosol from the microelectrode. Voltages in root epidermal cells were recorded under continuous superfusion with 5 mM $Ca^{2+}$-MES, pH 6.1, with 30 mM KCl. Current clamp recordings in guard cells used ±100 pA steps of 0.5 s with a 5-s cycle. Measurements were carried out in 5 mM $Ca^{2+}$-MES, pH 6.1, with 1 mM KCl to minimize background currents. Surface areas of impaled guard cells were calculated assuming a spheroid geometry (39) and voltages were analysed using Henry's EP Software Suite.

Current clamp offers advantages in quantifying small changes in conductance. Between the fully closed and fully open state of the stoma, the osmotic content of an *Arabidopsis* guard cell rises by approximately 200 to 300 mM on a cell volume basis (5). Roughly half of this osmotic content is made up of K+ transported across the plasma membrane and translates to approximately 70 fmol of K+ per guard cell. Assuming that 60 min are required for stomatal opening, the mean K+ flux needed to drive opening is 10 amol s-1, equivalent to a current of 0.9 pA. This value is below the limit of resolution for whole-cell voltage clamp measurements from plant cells. It represents less than 0.5% of the K+ currents typically recorded when *Arabidopsis* guard cells are clamped near the voltage extremes more than ±100 mV from the free-running voltage (5).

Total Protein and Total Starch Quantification

Leaves were harvested into liquid nitrogen and finely ground. 20 mg of material was weighed to extract total starch using Starch GO/B Assay kit (Sigma, Poole UK) according to the manufacturer's instructions. 10 mg of material was weighed to extract protein using homogenization buffer [0.0625M Tris.HCl pH 6.8, 1% (wt/vol) SDS, 10% (vol/vol) glycerol, and 0.01% (vol/vol) 2-mercaptoethanol]. Samples were incubated at 65° C. for 10 min before centrifuging at 13000 rpm for 10 min. Supernatant was collected and protein was quantified using Pierce BCA kit (Thermo Scientific, Loughborough, UK) according to the manufacturer's instructions.

Statistical Analysis

Statistically significance was determined by Student's t-test or ANOVA at $P<0.05$ using SigmaPlot12 (Systat) software. Data are reported as means±SE of n observations with the exception of stomatal assays which are reported as medians ±SE along with 0.25-0.75 ranges.

Example 2

We will construct a plasmid wherein a sequence encoding BLINK1 is inserted into a pSBII vector under the control of the constitutive promoter ZmUbi or a guard-cell specific promoter, such as the maize homologue of Myb60. The resulting plasmid will be inserted into the LBA4404 *A. tumefaciens* strain. The LBA4404 strain, with the integrated pSBIII plasmid will then be used to deliver e.g. the ZmUbi:BLINK1 expression cassette into maize. Transgenic T0, T1, and T2 plants will be grown in a greenhouse under a 16h-light/8h-dark condition. Transgenic positive and the sibling transgenic negative (i.e. wild type) plants can be determined in each generation by PCR analysis for the transgene. We will also measure growth, yield, water use efficiency and carbon assimilation in these plants.

For example, we will monitor the growth of plants by measuring rosette expansion and accumulation of dry biomass. We will also examine any increase in yield by measuring seed yield per plant.

Example 3

Figure 12:
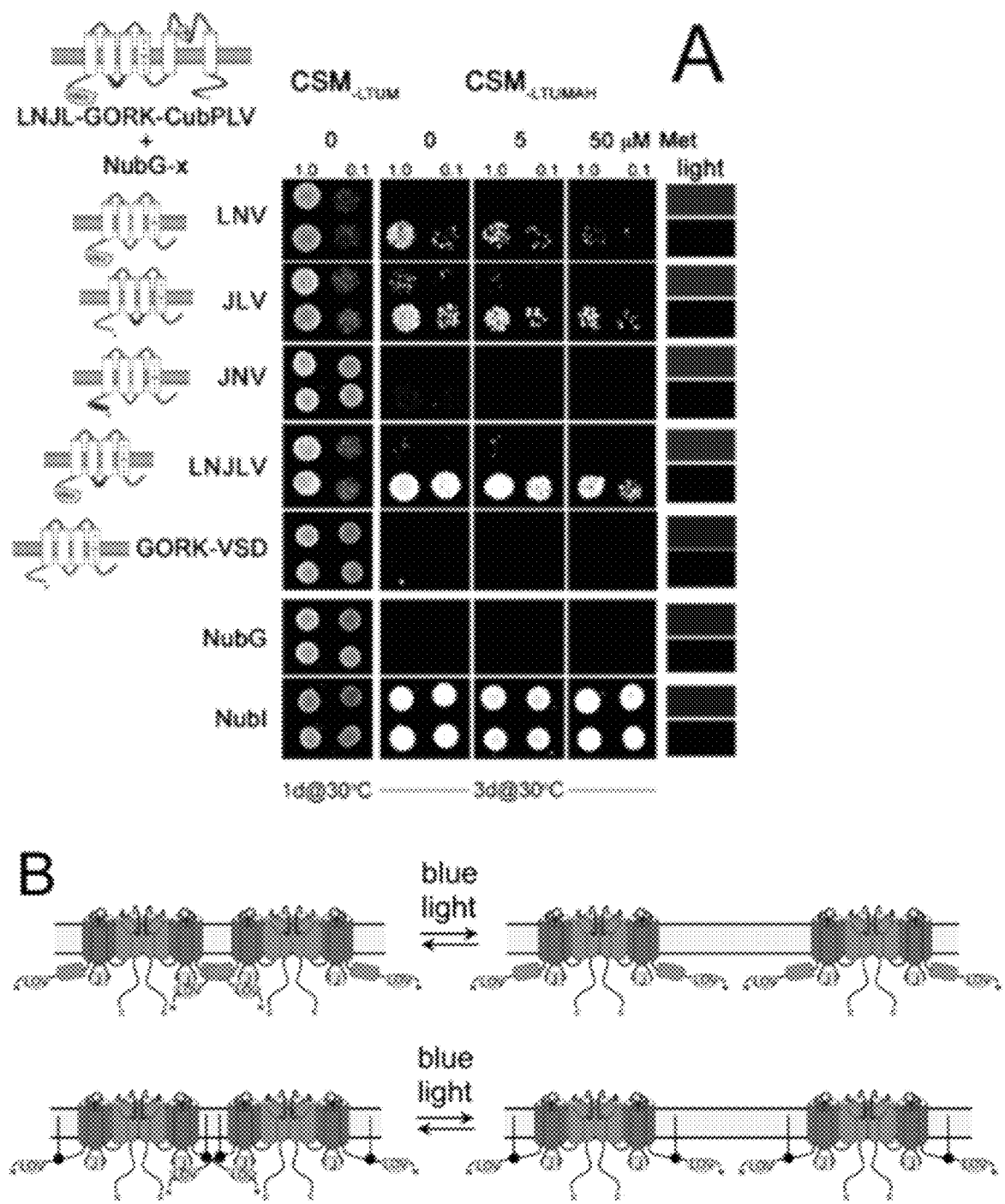
FIG. 12 shows that selected LOV2-Jα photoswitch components confer blue light dependence on GORK VSD interactions when separated between polypeptides. a) mbSUS assay using a GORK bait with LOV2 replacing the N-terminal binding domain and Jα helix replacing the S2-S3 loop. Various isolated VSDs with and without complementary photoswitch domains used as prey. Yeast were grown in the dark or under 50 μmol m$^{-2}$s$^{-1}$ blue light (right). Growth on 50 μM Met indicates strong interaction. b) Strategies to engineer LOV2 and Jα domains within a single GORK subunit using α-helical spacers (above) and myristoylated anchors (inverted black lollipops, below) to prevent LOV2-Jα interactions internal to each GORK tetramer.

GORK engineering for optogenetic K+ flux manipulation, The LOV2-Jα photoswitch reversibly photoactivates in blue light, displacing the Jα helix to uncage the LOV2 core. Several LOV-based optogenetic tools have been created using the Jα helix as a steric inhibitor that is released following photoactivation. All of these tools incorporate both components within a single polypeptide, linked by residues that serve as a 'hinge.' Our experiments, using an mbSUS assay and using GORK as a framework for insertions, show that the LOV2 and Jα domains have the potential to bind and release when incorporated in physically separate polypeptides (FIG. 12).

REFERENCES

1. A. M. Hetherington, F. I. Woodward, The role of stomata in sensing and driving environmental change. Nature. 424, 901-908 (2003).
2. S. Jasechko et al., Terrestrial water fluxes dominated by transpiration. Nature. 496, 347-350 (2013).
3. T. Lawson, M. R. Blatt, Stomatal Size, Speed, and Responsiveness Impact on Photosynthesis and Water Use Efficiency. Plant Physiology. 164, 1556-1570 (2014).
4. L. McAusland et al., Effects of kinetics of light-induced stomatal responses on photosynthesis and water-use efficiency. New Phytologist. 211, 1209-1220 (2016).
5. M. Jezek, M. R. Blatt, The Membrane Transport System of the Guard Cell and Its Integration for Stomatal Dynamics. Plant Physiology. 174, 487-519 (2017).
6. S. M. Assmann, T. Jegla, Guard cell sensory systems: recent insights on stomatal responses to light, abscisic acid, and CO2. Current Opinion in Plant Biology. 33, 157-167 (2016).
7. C. B. Engineer et al., CO2 Sensing and CO2 Regulation of Stomatal Conductance: Advances and Open Questions. Trends in Plant Science. 21, 16-30 (2016).
8. Y. Wang et al., Unexpected Connections between Humidity and Ion Transport Discovered Using a Model to Bridge Guard Cell-to-Leaf Scales. Plant Cell. 29, 2921-2939 (2017).
9. J. M. Christie, Phototropin Blue-Light Receptors. Annu. Rev. Plant Biol. 58, 21-45 (2007).
10. A. Takemiya, S. Inoue, M. Doi, T. Kinoshita, K. Shimazaki, Phototropins promote plant growth in response to blue light in low light environments. The Plant Cell. 17, 1120-1127 (2005).
11. C. Cosentino et al., Optogenetics. Engineering of a light-gated potassium channel. Science. 348, 707-710 (2015).
12. Z. Chen, C. Grefen, N. Donald, A. Hills, M. R. Blatt, A bicistronic, Ubiquitin-10 promoter-based vector cassette for transient transformation and functional analysis of membrane transport demonstrates the utility of quantitative voltage clamp studies on intact *Arabidopsis* root epidermis. Plant Cell Environ. 34, 554-564 (2011).
13. E. Cominelli et al., A guard-cell-specific MYB transcription factor regulates stomatal movements and plant drought tolerance. Current Biology. 15, 1196-1200 (2005).
14. J. M. Christie, J. Gawthorne, G. Young, N. J. Fraser, A. J. Roe, LOV to BLUF: Flavoprotein Contributions to the Optogenetic Toolkit. Mol Plant. 5, 533-544 (2012).
15. Y. Wang et al., Systems dynamic modeling of a guard cell Cl-channel mutant uncovers an emergent homeostatic network regulating stomatal transpiration. Plant Physiology. 160, 1956-1967 (2012).
16. T. Kinoshita et al., Phot1 and phot2 mediate blue light regulation of stomatal opening. Nature. 414, 656-660 (2001).
17. R. W. Pearcy, Sunflecks and photosynthesis in plant canopies. Annu. Rev. Plant Biol. (1990).

18. T. D. Sharkey, C. J. Bernacchi, G. D. Farquhar, E. L. Singsaas, Fitting photosynthetic carbon dioxide response curves for C(3) leaves. Plant Cell Environ. 30, 1035-1040 (2007).
19. J. Mattis et al., Principles for applying optogenetic tools derived from direct comparative analysis of microbial opsins. Nat Meth. 9, 159-172 (2012).
20. E. G. Govorunova, O. A. Sineshchekov, R. Janz, X. Liu, J. L. Spudich, Natural light-gated anion channels: A family of microbial rhodopsins for advanced optogenetics. Science. 349, 647-650 (2015).
21. V. Gradinaru et al., Molecular and cellular approaches for diversifying and extending optogenetics. Cell. 141, 154-165 (2010).
22. T. Doheny-Adams, L. Hunt, P. J. Franks, D. J. Beerling, J. E. Gray, Genetic manipulation of stomatal density influences stomatal size, plant growth and tolerance to restricted water supply across a growth carbon dioxide gradient. Philosophical Transactions of the Royal Society B: Biological Sciences. 367, 547-555 (2012).
23. J. Masle, S. R. Gilmore, G. D. Farquhar, The ERECTA gene regulates plant transpiration efficiency in *Arabidopsis*. Nature. 436, 866-870 (2005).
24. J. Hughes et al., Reducing stomatal density in barley improves drought tolerance without impacting on yield. Plant Physiology, pp. 01844.2016 (2017).
25. Y. Tanaka, T. Nose, Y. Jikumaru, Y. Kamiya, ABA inhibits entry into stomatal-lineage development in *Arabidopsis* leaves. The Plant Journal. 74, 448-457 (2013).
26. J. Negi et al., CO2 regulator SLAC1 and its homologues are essential for anion homeostasis in plant cells. Nature. 452, 483-486 (2008).
27. K. Kusumi, S. Hirotsuka, T. Kumamaru, K. Iba, Increased leaf photosynthesis caused by elevated stomatal conductance in a rice mutant deficient in SLAC1, a guard cell anion channel protein. Journal of Experimental Botany. 63, 5635-5644 (2012).
28. Y. Wang, A. Hills, M. R. Blatt, Systems analysis of guard cell membrane transport for enhanced stomatal dynamics and water use efficiency. Plant Physiology. 164, 1593-1599 (2014).
29. S. Bordage, S. Sullivan, J. Laird, A. J. Millar, & H. G. Nimmo, Organ specificity in the plant circadian system is explained by different light inputs to the shoot and root clocks. New Phytologist. 212, 136-149 (2016).
30. J. M. Christie, T. E. Swartz, R. A. Bogomolni, & W. R. Briggs, Phototropin LOV domains exhibit distinct roles in regulating photoreceptor function. Plant Journal. 32, 205-219 (2002).
31. E. Cominelli, et al. DOF-binding sites additively contribute to guard cell-specificity of AtMYB60 promoter. BMC Plant Biology. 11, 162 (2011).
32. A. M. Davis, A. Hall, A. J. Millar, C. Darrah, & S. J. Davis, Protocol: Streamlined sub-protocols for floral-dip transformation and selection of transformants in *Arabidopsis thaliana*. Plant Methods. 5, 3-7 (2009).
33. S. Sullivan, J. Petersen, L. Blackwood, M. Papanatsiou, & J. M. Christie, Functional characterization of Ostreococcus tauri phototropin. New Phytologist. 209, 612-623 (2015).
34. C. Grefen, & M. R. Blatt, A 2in1 cloning system enables ratiometric bimolecular fluorescence complementation (rBiFC). BioTechniques. 53, 311-314 (2012).
35. E. Kaiserli, S. Sullivan, M. A. Jones, K. A. Feeney, & J. M. Christie, Domain swapping to assess the mechanistic basis of *Arabidopsis* phototropin 1 receptor kinase activation and endocytosis by blue light. The Plant Cell. 21, 3226-3244 (2009).
36. G. Romani, et al. A virus-encoded potassium potassium channel is a structural protein in the chlorovirus Paramecium bursaria *chlorella* virus 1 virion. Journal of General Virology. 94, 2549-2556 (2013).
37. M. Papanatsiou, A. Amtmann, & M. R. Blatt, Stomatal Spacing Safeguards Stomatal Dynamics by Facilitating Guard Cell Ion Transport Independent of the Epidermal Solute Reservoir. Plant Physiology. 172, 254-263 (2016).
38. M. R. Blatt & C. L. Slayman, KCl leakage from microelectrodes and its impact on the membrane parameters of a nonexcitable cell. Journal of Membrane Biology. 72, 223-234 (1983).
39. M. R. Blatt, Electrical characteristics of stomatal guard cells: The ionic basis of the membrane potential and the consequence of potassium chlorides leakage from microelectrodes. Planta. 170, 272-287 (1987).
40. Y. Wang & M. R. Blatt, Anion channel sensitivity to cytosolic organic acids implicates a central role for oxaloacetate in integrating potassium flux with metabolism in stomatal guard cells. Biochemical Journal. 439, 161-170 (2011).

SEQUENCE LISTING

```
SEQ ID NO: 1 Kcv amino acid sequence
VFSKFLTRTEPFMIHLFILAMFVMIYKFFPGGFENNFSVANPDKKASWIDCIYFGVTTHS
TVGFGDILPKTTGAKLCTIAHIVTVFFIVLTL SEQ ID NO: 2 Kcv nucleic acid sequence
GTGTTTAGTAAATTTCTAACGCGAACTGAACCATTCATGATACATCTCTTTATTCTC
GCAATGTTCGTGATGATCTATAAATTCTTCCCGGGAGGGTTCGAAAATAACTTCTC
TGTTGCAAACCCGGACAAAAAGGCATCATGGATAGATTGTATATACTTCGGAGTAA
CGACACACTCTACTGTCGGATTCGGAGATATACTGCCAAAGACGACCGGCGCAAA
GCTTTGTACGATAGCACATATAGTAACAGTGTTCTTCATCGTTCTAACTTTATGA SEQ ID NO: 3 BLINK1 amino acid sequence
MGCTVSAELATTLERIEKNFVITDPRLPDNPIIFASDSFLQLTEYSREEILGRNCRFLQ
GPETDRATVRKIRDAIDNQTEVTVQLINYTKSGKKFWNLFHLQPMRDQKGDVQYFIG
VQLDGTEHVRDAAEREGVMLIKKTAEVFSKFLTRTEPFMIHLFILAMFVMIYKFFPGGF
ENNFSVANPDKKASWIDCIYFGVTTHSTVGFGDILPKTTGAKLCTIAHIVTVFFIVLTL
myristoylation sequence (my)
LOV2 domain and Jα(underlined)(L)
```

SEQUENCE LISTING

SEQ ID NO: 4 BLINK1 nucleic acid sequence
ATGGGATGTACAGTCTCTGCAGAGTTGGCTACTACACTTGAACGTATTGAGAAG
AACTTTGTCATTACTGACCCAAGGTTGCCAGATAATCCCATTATATTCGCGTCCG
ATAGTTTCTTGCAGTTGACAGAATATAGCCGTGAAGAAATTTTGGGAAGAAACT
GCAGGTTTCTACAAGGTCCTGAAACTGATCGCGCGACAGTGAGAAAAATTAGAG
ATGCCATAGATAACCAAACAGAGGTCACTGTTCAGCTGATTAATTATACAAAGA
GTGGTAAAAAGTTCTGGAACCTCTTTCACTTGCAGCCTATGCGAGATCAGAAGG
GAGATGTCCAGTACTTTATTGGGGTTCAGTTGGATGAACTGAGCATGTCCGAG
ATGCTGCCGAGAGAGAGGGAGTCATGCTGATTAAGAAAACTGCAGAAGTGTTTA
GTAAATTTCTAACGCGAACTGAACCATTCATGATACATCTCTTTATTCTCGCAATGT
TCGTGATGATCTATAAATTCTTCCCGGGAGGGTTCGAAAATAACTTCTCTGTTGCA
AACCCGGACAAAAAGGCATCATGGATAGATTGTATATACTTCGGAGTAACGACAC
ACTCTACTGTCGGATTCGGAGATATACTGCCAAAGACGACCGGCGCAAAGCTTTG
TACGATAGCACATATAGTAACAGTGTTCTTCATCGTTCTAACTTTATGA
myristoylation sequence (my)
~~~~~~~~~~~~~~~~~~~~~~~~~~~~
LOV2 domain and J<u>α(underlined)(L)</u>

SEQ ID NO: 5 Nucleic acid sequence of Myb60_TAIR10
CACAAGGACACAAGGACATATGGTATGATGATATGCTTTGTTTCTCTGCTTCTCTT
ACTAATTTGAAGCTGTTGGATTGATTTGTCTCTTCTTACGTCCCCTTCTTTTTTTTT
CGTTTTCTTTTGTCGTATAGACCAGGCAGGGGCTAGGGCCTAGTGATGGGTATTG
GCCCAATACTATTGGGTATTTGCCTGGTTTATTATTTCGATTTTAGGTTAATTCAA
TTTTAAGAATACGTAGATTTGTTTGGTTTAGTTTGGTTTGGTTGCACTAAGTTCGGT
TTTACATAAATAGAATCTAACACTACTAATTGTTATACGTAAAATACAACAACAATAA
CAGATTTTTCGTTTCAATTTTCGTTTAAGAGGGTAGACATTTTGGTTTGGTTTGG
TTCATTTTTTTTTTCCCTTTCAAATTCACATCCTTCACGTAGATGACAAAATAAAGAA
AAACATGAATGAAAGTTGTAACTTGTAAGCATCAACATGGAAATCATATCACAAAG
AACACAAATCTAACTAATGGGTCTTTTCACATATTGGTATAATTATAAGTTGTAAGA
ATATTAGTTAAACAGAGGCAACGAGAGATGCGTGATATATGAAAAGTTGAAAACAA
AAGACATGGATCTAAAGAGTCAAGCAAAATGTAATATCTTTTTTTCTTCTAAACTTG
AGGATGTCCAAGTTGCAGTGAATGATTCCCTTTAATCATGGAGAAATTCAATGAAA
TAATTGTGTTTCTTCCCACACTTTATCTTTATTTATTTTCTTACCACAATTACAACTA
TTATCACAAAAATGTAAGTAACATAGCTTGTGACTCTTCTTCCATTTATGAGTTGAT
TATCACTATATTTATAAGTAATTACCAACGAATGTTCCAAATTAAGCAAAATATTGTA
ATCGATACACTATGTATTCATCTACAATATGTTAACGAGCTCCTTTTATGGAAATAT
TTCGATTGAAAAAACATTTGATGGATCGTTCACTAAATAAATAATCCAGTAACGTTT
TCTTAAGGGAGATATACATATTCGTGTGGAGATCAACATATCTTCGTTAATTGACTA
CGCAAAATAGTTAATGGAAAAGGCAGAGTGACTCGTGAGCTTGGCAGATCCAAAA
GAGGTTGTCAAGAAAAAGCAGATTTAAAAGTTCTTCCCTCTTCTTTAAGTCACCCA
TTAATTTCACATATATGTACATACATGTTGCATTTAACTCATATACATAcatattctcacat
ctataaagagagcataagactcagagagatctagaggaagagagagagagaaagATG SEQ ID NO: 6 Nucleic acid sequence of Myb60 used for BLINK1
CACAAGGACACAAGGACATATGGTATGATGATATGCTTTGTTTCTCTGCTTCTCTT
ACTAATTTGAAGCTGTTGGATTGATTTGTCTCTTCTTACGTCCCCTTCTTTTTTTTT
CGTTTTCTTTTGTCGCATAGACCAGGCAGGGGCTAGGGCCTAGTGATGGGTATTG
GCCCAATACTATTGGGTATTTGCCTGGTTTATTATTTCGATTTTAGGTTAATTCAA
TTTTAAGAATACGTAGATTTGTTTGGTTTAGTTTGGTTTGGTTGCACTAAGTTCGGT
TTTACATAAATAGAATCTAACACTACTAATTGTTATACGTAAAATACAACAACAATAA
CAGATTTTTCGTTTCAATTTTCGTTTAAGAGGGTAGACATTTTGGTTTGGTTTGGTT
CATTTTTTTTTTCCCTTTCAAATTCACATCCTTCACGTAGATGACAAAATAAAGAAAA
ACATGAATGAAAGTTGTAACTTGTAAGCATCAACATGGAAATCATATCACAAAGAA
CACAAATCTAACTAATGGGCCTTTTCACATATTGGTATAATTATAAGCTGTAAGAAT
ATTAGTTAAACAGAGGCAACGAGAGATGCGTGATATATGAAAAGTTGAAAACAAAA
GACATGGATCTAAAGAGTCAAGCAAAATGTAATATCTTTTTTTCTTCTAAACTTGAG
GATGTCCAAGTTGCAGTGAATGATTCCCTTTAATCATGGAGAAATTCAATGAAATA
ATTGTGTTTCTTCCCACACTTTATCTTTATTTATTTTCTTACCACAATTACAACTATT
ATCACAAAAATGAAAGTAACATAGCTTGTGACTCTTCTTCCATTTATGAGTTGATTA
TCACTATATTTATAAGTAATTACCAACGAATGTTCCAAATTAAGCAAAATATTGTAAT
CGATACACTATGTATTCATCTACAATATGTTAACGAGCTCCTTTTATGGAAATATTT
CGATTGAAAAAACATTTGATGGATCGTTCACTAAATAAATAATCCAGTAACGTTTTC
TTAAGGGAGATATACATATTCGTGTGGAGATCAACATATCTTCGTTAATTGACTAC
GCAAAATAGTTAATGGAAAAGGCAGAGTGACTCGTGAGCTTGGCAGATCCAAAAG
AGGTTGTCAAGAAAAAGCAGATTTAAAAGTTCTTCCCTCTTCTTTAAGTCACCCATT
AATTTCACATATATGTACATACATGTTGCATTTAACTCATATACATACATATTCTCAC
ATCTATAAAGAGAGCATAAGACTCAGAGAGATCTAGAACTAGTGATATCACAAGTT
TGTACAAAAAAGCAGGCTTA SEQ ID NO: 7 Nucleic acid sequence of GC1
CTTCTACAAGAAGAGTAAAGATTCAGTAACCCGATGCTCCTGCTCTTCCTCAAGAC
CTTCCTTGATTCGCCGCCGGTATGTTCTCCGTCTGTGGTAGCGCCTTTGGAACAC
TCTACCAACGCCGCCATGAAAGGATCTCTCATGGCCGCAGGGGACGTGTTCTTCT
TACATCTGGTGTTAGGGCTATGGTTACTCCAGTGAGGAGGGAGAGGCAAGAGGTT
GCTTAATGATTCGTTTTTCCGGTGATACGAGAACTCTTTAGGTTTACCGGGAAGCT
TTTCCCATGAAAATGGGATGCCAAGTGGATGGAGAGGAGTTGCCGGAGAGTTGC

```
CGGAGAATAGGAGGGAATTGGAGGAGGAGGAAGAGAGTGATCGCCGGGTTGAAA
TGTTAACCGTCGAGGAGAATTTGACCGAGTTGGATCGTCTAGTAGGTACAATTCG
GGTCCTTGGCGAAGTATCCATTCAAAATAGTGTTTAGTTTTGGACTTGAGAACTTG
TTGTCTCTTTGATCTCTTTTATATAAAACTTTGGACGTGTAGGACAAACTTGTCAAC
ATAAGAAACAAAATGGTTGCAACAGAGAGGATGAATTTATAAGTTTTCAACACCGC
TTTTCTTATTAGACGGACAACAATCTATAGTGGAGTAAATTTTTATTTTGGTAAAAT
GGTTAGTGAATTCAAATATCTAAATTTTGTGACTCACTAACATTAACAAATATGCAT
AAGACATAAAAAAAGAAAGAATAATTCTTATGAAACAAGAAAAAAAACCTATACAA
TCAATCTTTAGGAATTGACGATGTAGAATTGTAGATGATAAATTTTCTCAAATATAG
ATGGGCCTAATGAAGGGTGCCGCTTATTGGATCTGACCCATTTTGAGGACATTAAT
ATTTTCATTGGTTATAAGCCTTTTAATCAAAATTGTCATTAAATTGATGTCTCCCTCT
CGGGTCATTTTCCTTTCTCCCTCACAATTAATGTAGACTTTAGCAATTTGCACGCT
GTGCTTTGTCTTTATATTTAGTAACACAAACATTTTGACTTGTCTTGTAGAGTTTTC
TCTTTTATTTTTCTATCCAATATGAAAACTAAAGTGTTCTCGTATACATATATTAAA
ATTAAAGAAACCTATGAAAACACCAATACAAATGCGATATTGTTTTCAGTTCGACGT
TTCATGTTTGTTAGAAAATTTCTAATGACGTTTGTATAAAATAGACAATTAAACGCC
AAACACTACATCTGTGTTTTCGAACAATATTGCGTCTGCGTTTCCTTCATCTATCTC
TCTCAGTGTCACAATGTCTGAACTAAGAGACAGCTGTAAACTATCATTAAGACATA
AACTACCAAAGTATCAAGCTAATGTAAAAATTACTCTCATTTCCACGTAACAAATTG
AGTTAGCTTAAGATATTAGTGAAACTAGGTTTGAATTTTCTTCTTCTTCTTCCATGC
ATCCTCCGAAAAAAGGGAACCAATCAAAACTGTTTGCATATCAAACTCCAACACTT
TACAGCAAATGCAATCTATAATCTGTGATTTATCCAATAAAAACCTGTGATTTATGT
TTGGCTCCAGCGATGAAAGTCTATGCATGTGATCTCTATCCAACATGAGTAATTGT
TCAGAAAATAAAAGTAGCTGAAATGTATCTATATAAAGAATCATCCACAAGTACTA
TTTTCACACACTACTTCAAAATCACTACTCAAGAAAT

SEQ ID NO: 8: BLINK 1 variant (myLK) amino acid sequence
MGCTVSAELATTLERIEKNFVITDPRLPDNPIIFASDSFLQLTEYSREEILGRNCRFLQ
GPETDRATVRKIRDAIDNQTEVTVQLINYTKSGKKFWNLFHLQPMRDQKGDVQYFIG
VQLDGTEHVRDAAEREGVMLIKKTAENIDEAAKELPDANLRPEDLWANHSVFSKFLT
RTEPFMIHLFILAMFVMIYKFFPGGFENNFSVANPDKKASWIDCIYFGVTTHSTVGFGDI
LPKTTGAKLCTIAHIVTVFFIVLTL
myristoylation sequence (my)
LOV2 domain and Jα(underlined) (L)

SEQ ID NO: 9 BLINK 1 variant (myLK) nucleic acid sequence
ATGGGATGTACAGTCTCTGCAGAGTTGGCTACTACACTTGAACGTATTGAGAAG
AACTTTGTCATTACTGACCCAAGGTTGCCAGATAATCCCATTATATTCGCGTCCG
ATAGTTTCTTGCAGTTGACAGAATATAGCCGTGAAGAAATTTTGGGAAGAAACT
GCAGGTTTCTACAAGGTCCTGAAACTGATCGCGCGACAGTGAGAAAAATTAGAG
ATGCCATAGATAACCAAACAGAGGTCACTGTTCAGCTGATTAATTATACAAAGA
GTGGTAAAAAGTTCTGGAACCTCTTTCACTTGCAGCCTATGCGAGATCAGAAGG
GAGATGTCCAGTACTTTATTGGGGTTCAGTTGGATGGAACTGAGCATGTCCGAG
ATGCTGCCGAGAGAGAGGGAGTCATGCTGATTAAGAAAACTGCAGAAAATATT
GATGAGGCGGCAAAAGAACTTCCAGATGCTAATTTGAGACCAGAGGATTGTGG
GCTAACCACTCAGTGTTTAGTAAATTTCTAACGCGAACTGAACCATTCATGATACA
TCTCTTTATTCTCGCAATGTTCGTGATGATCTATAAATTCTTCCCGGGAGGGTTCG
AAAATAACTTCTCTGTTGCAAACCCGGACAAAAAGGCATCATGGATAGATTGTATA
TACTTCGGAGTAACGACACACTCTACTGTCGGATTCGGAGATATACTGCCAAAGA
CGACCGGCGCAAAGCTTTGTACGATAGCACATATAGTAACAGTGTTCTTCATCGTT
CTAACTTTATGA
myristoylation sequence (my)
LOV2 domain and Jα(underlined) (L)

SEQ ID NO: 10 GORK amino acid sequence
MGRLRRRQEI IDHEEEESND DVSSRRGKLS LAETFRWLDS SEHRRIETDG
HNDYKYIIHP KNRVVYKAWEM FILVWAIYSS LFTPMEFGFF RGLPERLFVL
DIVGQIAFLV DIVLQFFVAY RDTQTYRTVY KPTRIAFRYL KSHFLMDFIG
CFPWDLIYKA SGKHELVRYL LWIRLFRVRK VVEFFQRLEK DTRINYLFTR
ILKLLFVEVY CTHTAACIFY YLATTLPPEN EGYTWIGSLK LGDYSYENFR
EIDLWKRYTT ALYFAIVTMA TVGYGDIHAV NLREMIFVMI YVSFDMVLGA
YLIGNITALI VKGSNTERFR DKMNDLISFM NRKKLGRDLR SQITGHVRLQ
YDSHYTDTVM LQDIPASIRA KIAQLLYLPY IKKVPLFKGC STEFINQIVI
RLHEEYFLPG EVITEQGNVV DHLYFVCEGL LEALVTKTDG SEESVTLLGP
HTSFGDISII CNISQPFTVR VCELCHLLRL DKQSFSNILE IYFHDGRTIL
NNIMEEKESN DRIKKLESDI VIHIGKQEAE LALKVNSAAF QGDFYQLKSL
IRSGADPNKT DYDGRSPLHL AACRGYEDIT LFLIQEGVDV NLKDKFGHTP
LFEAVKAGQE GVIGLLVKEG ASFNLEDSGN FLCTTVAKGD SDFLKRLLSS
GMNPNSEDYD HRTPLHVAAS EGLFLMAKML VEAGASVISK DRWGNSPLDE
ARLCGNKKLI KLLEDVKNAQ SSIYPSSLRE LQEERIERRK CTVFPFHPQE
AKEERSRKHG VVVWIPSNLE KLIVTAAKEL GLSDGASFVL LSEDQGRITD
IDMISDGHKL YMISDTTDQT
```

SEQUENCE LISTING

SEQ ID NO: 11 GORK genomic sequence
```
CTAGACAAAA CCTTACGTTA TACACTTCAA CTAATAAAGA GTCCAAACCA
AACAAAAAAA AAACAGTAGT TTCTCGACAG AAACAAAATC AATATAGCTT
TAACATCACG AGAAAGAAGA ACTAAAGAAG ACCAAACAAA AAATAATTTG
GAAAAAAACA GAGAAGCAGC TCTCGTGATC TTCCCGCCTT TTCTCTTCAA
CTTGTAAAAC ATTACAAGAT CTATCTTCTA CCAAAAAGAC GAAGTTTCGA
GTGTCAGATT CAAGAGTTGA ATCGGGTATT AAACTCTGTT TTTCTAGATC
TTTGTGTCGA AGAGATCGCC GGAGATTTCA TTTAACCGAT TCTTGAAAAC
ATGGGACGTC TCCGGAGACG GCAAGAGATA ATAGATCATG AAGAAGAGGA
ATCAAACGAC GACGTTTCAT CAAGAAGAGG AAAACTCAGT TTAGCCGAGA
CGTTTCGGTG GCTTGATTCA TCAGAGCATC GGAGAATTGA AACCGATGGT
CATAATGATT ATAAATACAT CATTCATCCC AAAAACAGGT TCTTTCTTTT
TTCTCTTTCT TCATCATGCA CTTGAAGAGT TTCCTTTCTA TCGGGAGATA
AATACGTAGA AAATACTTTT CTTGAAACCT TCAAAATATC TTCTGTTTTT
TTTTCTGTAA CTTCAGAAAA AAACTTTATT CACCATACCA CTTCAAAAAC
TTGTCTCCCT AGTTTTAACT TCGAATAATA CAATAATAGA AAATTCACCA
TTTTAATAAT TATCAATCAC TAAAACTCTT ATCGTTATTT CTTTCTGCTC
ATTTTTAAGG CTGTGTCACC AATCTAATCT AATATTAGTA TCACTTCAAT
CTAGTTTAAA TATTAATATT TATGTCAAGG ATTTTTTAAA ACAACTAAAT
GATTTAAGGT TCGAAAAATT ACGATAATTA GAATGGACAA ATCCGTTTAC
AGTTTGGATT GCTTTTTATT TACCGTTCAT AAAGTATAAT TTATAGTAAT
ACAAAATAAT AAAAATAGAA TCCGTCTACA ATGGACTAAC GATATATCTT
TTTTACGTAA AAGTGAATTT GGTCTACAGA ATTTATTGTT CGCTCTAAAA
ATAAAATGGT CTAATCGCTT AATTCGTATC ATCCATTAAT AGCCTTAGGA
TTTAGATGAA TAATCTTCAT CACTTATCAA AAGTAGATAT TAGATGCTAA
TCAGGTGATT TTGTTGTCGA TATTCTTTTC ATTATTATTT ACTAAGAAAA
AAGAAATTGG TGGGACACTT CCTTGTGATA TATTCTTCT CTTTCGTTGT
CCACTGATCA CCTCAATCTA AGCATTTGTT TTATTTGCAG CCGACCTATT
GAAAATTTAA AACTTAAATC TAAAACCAAA TTCCGACCAA AACAAGGAAA
AACTTTAAAT CTATCTTTAA ATAGAATCCT ACGTTAAATT GCACCAGGAA
TAAAAAAAAA AATACTACGT TAAACAACTT GAATCCACTA GAGGATACTG
TTACACTCCC ATAAATGTTT CACTAGGGTT ATATTAGTAA TTATGCGTTG
TGACAGAATC ATCGAAGATC GGATTATTAA TTGGTTCCAC TAAAGCTGCC
GTAACCAGAG GCCACACGTG GATATTTCAT CCACCTGTTC TTCTAAGCAT
AATAACATTA ACTATAAAAT AACAAAACTA TACTAGTGAA AATGTATATT
CAACTTAGTC CAGCTATGTC GATCTTAAAC AAATAAAATT TAAAACGTTG
TTGCTTGCAC TTAACTAATA ACTATAGTAT TATTTTCATT TGTCTCCTTC
CCACGATTCC GTTTAGCTAC ATTACCAATT TGACGAATCA AGTATAAGCC
ACAATCTTTA CATTTTCAAG AATCTTTGAT TAGACCTGAA TTAATGAAAA
GTGAGAAGAA ATTGATCAGG TGGTACAAGG CATGGGAAAT GTTTATATTG
GTGTGGGCAA TATACTCCTC ATTGTTCACT CCCATGGAGT TTGGTTTCTT
CCGCGGTCTG CCTGAGAGAC TCTTTGTACT TGACATTGTT GGTCAGATCG
CGTTCTTGGT CGATATTGTT CTTCAGTTCT TTGTTGCCTA TCGCGATACT
CAGACCTACC GGACTGTCTA CAAACCAACA CGTATTGCTT TCCGGTCAGT
TATATATATT AGACTCTTAC AATCATTTTA ACCATTTCTA CTTATATAGC
CTTTAATGGA GGAAGTATGT CTTTCATCAG GTACTTGAAG TCGCATTTTC
TCATGGATTT CATCGGTTGC TTCCCTTGGG ATCTTATTTA TAAGGTACTT
AACTTTGCTT TTGATATTTG CTTAGATCTT CAACAAAAGT CAAACCAAAG
AAACACTATA GCTTATAAAT ATTTCTTGGT TTATAAAAAC TCAAACCAAA
TAAACACTAT TTGTAATTTG TTTGGTTCGT TTCTAGGTGA TGCAACTTTA
GTTCCTACTT GATGCAATTT TAGCTTAGTT AGGTTGGAAA TTTTGTAAAA
GTAACTTTGA AACATATAAA AATATTTCTT AACTAATATT ATATTTATCT
AATATGATAA CACATATTAT AATTTCTTAT ATAATTAAAA TAAAATTCAC
ATAAATATCA ATTCATTTGG TTAGTTTACA CTAAAATCAG TTTCACTTCG
ATTTCGATGT TTAAATAATA AACCAATTGG GTTATTTAAA TACATTTTTG
GTTCTGATTC GGTTTGGTTT GGTTTATACT CCTACCCTAA CCTTTTTGTA
GGCATCAGGG AAACATGAGT TGGTGAGGTA CTTGTTGTGG ATAAGGCTAT
TTCGGGTTCG CAAAGTGGTT GAGTTTTTCC AAAGGCTTGA GAAAGACACA
AGAATCAACT ATCTATTCAC TAGAATCTTA AAGCTCTTGT TCGTTGAAGT
TTATTGTACT CACACTGCTG CTTGTATCTT CTATTACTTG GCCACCACTC
TTCCTCCAGA AAACGAAGGT TACACTTGGA TCGGTAGCTT GAAGCTAGGA
GACTATAGCT ACGAGAATTT CCGAGAAATC GATCTCTGGA AACGTTATAC
TACCGCTCTA TACTTCGCCA TTGTCACTAT GGCAACTGTC GGTATAAAAA
CCAATTCTAT TTTGATGCTA ATTTAATTAG TTACTAACAA AGAGATTGAT
GGGTTTTTTT TTTTTCGTTT TGGTTTTAGG TTATGGAGAA ATTCACGCGG
TGAATCTGAG GGAAATGATA TTCGTGATGA TATATGTTTC GTTTGATATG
GTTCTCGGTG CTTACCTTAT TGGTAACATC ACTGCCTTGA TTGTGAAAGG
TTCAAACACA GAGAGGTTCA GAGATAAAAT GAATGATCTC ATAAGTTTCA
TGAACCGCAA AAAACTCGGG AGAGACCTTC GTAGCCAGAT AACTGGTCAT
GTTAGATTGC AGTACGACAG TCACTACACC GACACTGTCA TGCTTCAGGA
CATCCCAGCA TCAATCCGCG CCAAGGTACC CTAATTATAA AAACAAAATT
CTCGTTTTGT TACCAACAAA TATTCATGTA CTTTTTAGGT TAGAGTTAGT
GTTTCTTGGA ACACAATCTT TGTCAAGCCG GTCCGCATAA CCCGCTCAAT
ATCTTAGCCT GCTGCATGAC GGATTAGCGC GCATTGACAC CCTAACTAAT
ACACATTTTT CTTGCAGATT GCGCAATTAT TGTATCTGCC TTACATCAAA
AAAGTTCCTC TCTTCAAAGG CTGCTCCACA GAGTTTATTA ATCAAATAGT
```

```
                           SEQUENCE LISTING
TATAAGGCTC CATGAAGAGT ATTTTCTTCC AGGAGAAGTA ATAACAGAGC
AAGGAAACGT CGTGGATCAT TTGTATTTCG TCTGTGAAGG CTTACTGGTA
CGTAAAATCT CATTGTGCTT GTGTCTATCT TTGCTTCTTG TATGTCTCAC
TTTGTAATTT TTGGGGATTT TTATAGGAGG CTCTTGTTAC AAAAACAGAT
GGATCAGAAG AGAGTGTGAC GTTACTTGGG CCTCACACTT CTTTTGGAGA
CATCTCCATC ATTTGCAACA TTTCTCAACC TTTCACTGTT AGGGTTTGTG
AGCTATGCCA TCTTTTACGA CTCGATAAAC AGTCTTTCTC AAACATCCTC
GAGATTTATT TTCACGACGG ACGCACAATC TTGAACAATA TTATGGAGGT
ACTCTTTTTT CTATCTCTTA CTTAGGGTTT TGAAACTCGA TTGAGAAATC
TTGCAACTCA CTCAAACTTG GTTTTGGCAG GAGAAGGAAT CAAATGATAG
GATAAAGAAG CTAGAATCTG ACATAGTGAT TCACATTGGG AAACAAGAAG
CAGAACTTGC ATTGAAAGTA AACAGTGCAG CTTTCCAAGG AGATTTTTAC
CAGCTTAAGA GCTTAATCCG ATCTGGAGCC GATCCTAACA AAACCGATTA
CGATGGAAGA TCACCGCTTG TACGTTTGTC GCTTATCGAT TATCTTTCTT
TTAAGAGCTT AACTTTGATT CTTTTTTATA TCCAGCATCT TGCAGCATGT
AGAGGCTATG AAGACATTAC ATTATTCCTT ATTCAGGAGG GTGTTGATGT
CAATCTAAAA GGTAAATATT GAATCGTTCT AATGGAAAAC ATTACATTGT
TTTATGTTTA CGCTTTTGAT CACAAATTTT CGCAGATAAG TTCGGACACA
CACCATTGTT TGAGGCTGTG AAAGCAGGAC AAGAAGGAGT GATTGGTTTG
CTTGTCAAAG AAGGAGCCTC CTTTAATTTA GAAGATTCAG GAAACTTCCT
TTGCACGACA GTTGCTAAAG GCGACTCTGA TTTTCTCAAG AGATTGCTTT
CAAGCGGTAT GAACCCAAAC AGTGAAGATT ATGATCACAG AACGCCGCTT
CATGTCGCGG CTTCTGAAGG GTTATTCTTG ATGGCTAAAA TGTTGGTTGA
AGCTGGAGCA AGCGTTATTT CTAAAGACCG GTAAAAATCA TGCAAAATGA
ATCATTTAAT TCTTTAAAAC TATAGTTTAT AGACTTCATA ACTTCTCTCT
TTGAAGATGG GGGAATTCTC CGCTTGATGA AGCCCGATTG TGCGGAAACA
AGAAACTGAT TAAGTTACTC GAAGATGTGA AAAATGCTCA GTCGTCTATC
TACCCGTCAA GCTTGCGTGA ATTACAAGGT ACTCGTATAC TTCCTTCAGA
CGATACAACT CAAAAATGGA TCTTGTAATT CTTGAATTTG ATTTATGTTT
TGAAAAACAG AGGAGAGAAT TGAGAGACGA AATGCACGG TGTTTCCATT
CCACCCGCAA GAGGCGAAAG AAGAGCGTAG TAGAAAGCAC GGAGTTGTGG
TTTGGATCCC AAGCAATCTC GAGAAACTCA TAGTAACCGC TGCGAAAGAG
CTAGGGCTAT CGGATGGAGC CTCATTTGTA CTATTATCAG AAGACCAAGG
TCGTATCACA GACATTGATA TGATTAGTGA TGGACACAAA TTGTATATGA
TCAGTGATAC TACTGATCAA ACATAATGAT GGACTCTTCG ATTTTTCCGA
TGATTCATTT GAGGTTTTTA TATTCTAGAG CATTTTGACA CA

SEQ ID NO: 12: CER6 promoter sequence
TAGTGCTTTATATATGTTTGATACTTCTGTTTGGCAATATCAATCATAGT
AGAAAAGATATGGACTTCATTTGAGGTTTTTGGTGGATTGTGTCTATATG
TGAAATCATGGGATCTCAAGATTTGTCTGCATTCAGTTTCCAAGTCAAAC
ATCGTAACTA CTGTTTGATT TTCCCTCATG CTTGCAGTTT TCATGGATAT
CTCAAGATTT GTCTTCTTGC ACTTTCCAAG TCAAACATAA AGTAACTACT
GATTGATATT CCCTCGTGTA TTACCCTCTT TCAAATGACA CAATTGGGCC
CAAGTAGAGG AATTTCATAG TGAATTCAAA AGATTAACTG TATTCCACCG
TCGTATTTTG ATAACATTTA GTTATTCCTT TTCTTTTTTT TCTTCTGCAA
CAGTTTTTTT TTAATACATT TAGTGTTGGT TTGGTTCAAT GAAATATTAT
ATGTTACTTC TTTTTTTGGA AATAAATTAT TCATTCTTTC TACTATAAAA
GGAATTGTTC ATGCTTTTTT GATACAATAG TATACCATTT CAAAAGATAC
CATAGACCAG TTATTACATG AATCGCCAAA ACAACACTAA AATCAGAAAA
TCAGTATATT TTGGTATAGT CTCCAACATA CAATCATAAA ACCTCTGTGA
AATTTAAAAT CTATATTTGA CATTTCAAAG TTTAACAACA TAGTTCTAAA
TAATTACCTA AATTTAAGT CAAATGTGAA TTATATTTA CTCTTCGATA
TCGGTTGTTG ACGATTAACC ATGCAAAAAA GAAACATTAA TTGCGAATGT
AAATAACAAA ACATGTAACT CTTGTAGATA TACATGTATC GACATTTAAA
CCCGAATATA TATGTATACC TATAATTTCT CTGATTTTCA CGCTACCTGC
CACGTACATG GGTGATAGGT CCAAACTCAC AAGTAAAAGT TTACGTACAG
TGAATTCGTC TTTTTGGGTA TAAACGTACA TTTAATTTAC ACGTAAGAAA
GGATTACCAA TTCTTTCATT TATGGTACCA GACAGAGTTA AGGCAAACAA
GAGAAACATA TAGAGTTTTG ATATGTTTTC TTGGATAAAT ATTAAATTGA
TGCAATATTT AGGGATGGAC ACAAGGTAAT ATATGCCTTT TAAGGTATAT
GTGCTATATG AATCGTTTCG CATGGGTACT AAAATTATTT GTCCTTACTT
TATATAAACA AATTCCAACA AAATCAAGTT TTTGCTAAAA CTAGTTATT
TGCGGGTTAT TTAATTACCT ATCATATTAC TTGTAATATC ATTCGTATGT
TAACGGGTAA ACCAAACCAA ACCGGATATT GAACTATTAA AAATCTTGTA
AATTTGACAC AAACTAATGA ATATCTAAAT TATGTTACTG CTATGATAAC
GACCATTTTT GTTTTTGAGA ACCATAATAT AAATTACAGG TACGTGACAA
GTACTAAGTA TTTATATCCA CCTTTAGTCA CAGTACCAAT ATTGCGCCTA
CCGGGCAACG TGAACGTGAT CATCAAATCA AAGTAGTTAC CAAACGCTTT
GATCTCGATA AAACTAAAAG CTGACACGTC TTGCTGTTTC TTAATTTATT
TCTCTTACAA CGACAATTTT GAGAAATATG AAATTTTTAT ATCGAAAGGG
AACAGTCCTT ATCATTTGCT CCCATCATT GCTTTTGTCT AGTTACAACT
GGAAATCGAA GAGAAGTATT ACAAAAACAT TTTTCTCGTC ATTTATAAAA
AAATGACAAA AAATTAAATA GAGAGCAAAG CAAGAGCGTT GGGTGACGTT
GGTCTCTTCA TTAACTCCTC TCATCTACCC CTTCCTCTGT TCGCCTTTAT
ATCCTTCACC TTCCCTCTCT CATCTTCATT AACTATCTT CAAAATACC
CTAATCACAT TTTGTAACAA TAATACAATT ATACATTAAA ACTCTCCGAC
```

SEQUENCE LISTING

GATG

SEQ ID NO: 13: TaGSTA1 promoter sequence
tggga ggaggccttg gatgttgatc tccatttata cacagagcag ggagcaccac acccggcccg cgtggcccaa
ggaaataaca aggctacatc gacttttag ctagtgtctagatctgcttt atttcatttc taccaaaaaa gatatatgaa
atgatgagtg ccaaattaaatgagctcttg aatcatttaa accgggtaag taatcatctt tgttagttta
tcgatactccctctattcca tattgtggtg cgaaggaagt aagtactagt tagaaacacg
tgcgttggtacggattggag aaacaactac tccctccatt cactttttgta gatcgcggaa
ccaatttccgacagcccccc aaacatcggt gaaggaccaa tataccccag atagatagat
ttgaaattcaaattactcca catcgatcgc gcccttcctc ccatcgtcga ggtctcaata tcagaactggatcctctaac
gtggagaagg gaaggcaggt aagcgacagt agtcagctag tctaaaatgaagaaacaaag tcagagaact
gtagcaaaac actgtaaatc aacttgctac tattacgtcgctagcagttg gcccattgat ttagcaagtg
gtaggcgaca tacagtgtca cttgagcaagtgtaaaggta aaagagactt tacatgcatg gcggctatcc
ggctgccgac atattccaacatggaagatt tttcgctagc tctaccaggc cacgatattc caacgcggga
agataatcgtgtccgcacaacttatttgaggcttgagagagatggtagcaccaaaagcaatgtgccctctcgttgtctcga
aaacactaagggtgggtatatgcatatcttattaactaaaaaaggtagaaaaatgcctctaatttaaaatcaacaagtaaa
tgtacattccaatatgattttcgttgtcactcaattgaataattttcactatcgatggaaatgtatttttttttaatctttgttctgattca
gttgaatgctataagttccgagagttaagcttgccagcgatcaatcattttcccacttgccaacgccttgcatgttctataaaa
aatcaacttggatgctattattacatcgctagcagttggcccattggtaggcgacacatcacttttccatggctctaaatgttcc
tgtttgatgcttgtgccttaatagcaagacagactttccacggctctggctctcaccagctgcgagatatttgccaaatagtt
cgtttggctagagtgtggaataacttattctactcttaaacacaaagtgttaaatcactctctccatatataactaaactacaat
gttgtataaaagatacatcgagaaggttttacgtttatcctacaactttgatcctaataataatcattacatagcacaaccttc
cgtaggcaaaacacctcacgaggtttggtgttgctccaaaagatctctttatcaagactagttagtataactctttaaagttaa
actaaatcatgcatgtgaagaacattcagatttactgtgcatataaatcttctaaactaaaaaaaatcacatataattttgatt
gtaagcaattatagtagatggatatcacacatatattttttgcaagttaatttagatcaaaataatctgaatcaggtggatgtg
aagaaggaaagttaaagtacttagcataccggacttgcctcctccacgttccaggatccagttccctagctagcagccta
gcacctcgttgatcacgccacgccccgttcccagaacctggccaattgataggccaaatagcacctggcctcactgatct
ccccaggactcggatctcttcgccaatcgatcggctagcacctaactggcctcaccgattgtcctagcagcagcacgccg
gtcggcgactccaccccgcagcagaacgccagccggcgaccccaccccgcaacagaacgtcagccggcgacc
cccacccagaaggagcagatcgccggtgagggagaaggtcagcgcgtcgccatcgcccctggttctactcgcccaa
cacccgccagaccaggtgctgctcgtcatccagtcacctcgccgatccagggctagtgatctagtctgccgagggcttgg
gacctgggggctgtcggctccacttcggcgtc

The invention claimed is:

1. A method of increasing at least one of growth, yield, drought tolerance, water use efficiency and/or carbon assimilation in a plant, the method comprising expressing a light-gated potassium channel in cells of the stomatal complex of the plant, wherein the method comprises introducing and expressing in the plant a nucleic acid construct comprising a nucleic acid sequence encoding a blue-light gated potassium channel with the amino acid sequence defined in SEQ ID NO: 3 or a functional variant thereof comprising one or more amino acid substitutions, deletions and/or additions compared to the sequence defined in SEQ ID NO: 3, said functional variant having at least 95% overall sequence identity to the sequence defined in SEQ ID NO: 3, and the blue-light gated potassium channel or the functional variant thereof being operably linked to a regulatory sequence comprising a guard-cell specific promoter.

2. The method of claim 1, wherein the method increases both water use efficiency and carbon assimilation.

3. The method of claim 1, wherein the nucleic acid construct comprises a sequence as defined in SEQ ID NO: 4 or the nucleic acid construct comprises a sequence encoding the functional variant of the blue-light gated potassium channel with the amino acid sequence defined in SEQ ID NO: 3, said functional variant comprising one or more amino acid substitutions, deletions and/or additions compared to the sequence defined in SEQ ID NO: 3, and wherein said functional variant has at least 95% overall sequence identity to the sequence defined in SEQ ID NO: 3.

4. The method of claim 1, wherein the plant is a monocot or dicot.

5. A nucleic acid construct comprising a nucleic acid sequence encoding a blue-light gated potassium channel with the amino acid sequence defined in SEQ ID NO: 3 or a functional variant thereof, said functional variant having at least 95% overall sequence identity to the sequence defined in SEQ ID NO: 3 and comprising one or more amino acid substitutions, deletions and/or additions compared to the sequence defined in SEQ ID NO: 3, operably linked to a regulatory sequence, wherein the regulatory sequence is a stomatal complex promoter, and wherein the stomatal complex promoter is a guard-cell specific promoter.

6. The nucleic acid construct of claim 5, wherein the nucleic acid sequence encoding the blue-light induced potassium channel comprises a sequence as defined in SEQ ID NO: 4 or the nucleic acid construct comprises a sequence encoding the functional variant of the blue-light gated potassium channel with the amino acid sequence defined in SEQ ID NO: 3, said functional variant said functional variant having at least 95% overall sequence identity to the sequence defined in SEQ ID NO: 3 and comprising one or more amino acid substitutions, deletions and/or additions compared to the sequence defined in SEQ ID NO: 3.

7. The nucleic acid construct of claim 5, wherein the guard-cell specific promoter is selected from Myb60, GC1 and SNAC1.

8. A vector comprising the nucleic acid construct of claim 5.

9. A host cell comprising the vector of claim 8.

10. A transgenic plant expressing the vector of claim 8.

11. The transgenic plant of claim 10, wherein the plant is a monocot or dicot.

12. A method of producing a transgenic plant, the method comprising:
  a. selecting a part of the plant;
  b. transfecting at least one cell of the part of the plant of part (a) with the vector of claim 8; and
  c. regenerating at least one plant derived from the transfected cell or cells.

13. A plant obtained or obtainable by the method of claim 12, wherein the plant comprises the nucleic acid construct.

14. The plant of claim 13, wherein the plant is a monocot or dicot.

* * * * *